(12) United States Patent
Wang

(10) Patent No.: US 12,267,990 B2
(45) Date of Patent: Apr. 1, 2025

(54) SHIELDING COVER AND DISPLAY DEVICE

(71) Applicants: K-Tronics (Suzhou) Technology Co., Ltd., Suzhou (CN); BOE Technology Group Co., Ltd., Beijing (CN)

(72) Inventor: Di Wang, Beijing (CN)

(73) Assignees: K-Tronics (Suzhou) Technology Co., Ltd., Suzhou (CN); BOE Technology Group Co., Ltd, Beijing (CN)

( * ) Notice: Subject to any disclaimer, the term of this patent is extended or adjusted under 35 U.S.C. 154(b) by 316 days.

(21) Appl. No.: 17/772,771

(22) PCT Filed: May 12, 2021

(86) PCT No.: PCT/CN2021/093316
§ 371 (c)(1),
(2) Date: Apr. 28, 2022

(87) PCT Pub. No.: WO2022/001389
PCT Pub. Date: Jan. 6, 2022

(65) Prior Publication Data
US 2022/0377951 A1    Nov. 24, 2022

(30) Foreign Application Priority Data
Jun. 29, 2020  (CN) .......................... 202010606789.0

(51) Int. Cl.
*G06F 1/16* (2006.01)
*C07D 209/08* (2006.01)
(Continued)

(52) U.S. Cl.
CPC ......... *H05K 9/0054* (2013.01); *C07D 209/08* (2013.01); *C07D 209/10* (2013.01);
(Continued)

(58) Field of Classification Search
CPC ...... H05K 9/0054; H05K 5/03; G06F 1/1656; G06F 1/182
See application file for complete search history.

(56) References Cited

U.S. PATENT DOCUMENTS

| 6,189,850 B1 * | 2/2001 | Liao .......................... G06F 1/16 |
| | | 248/920 |
| 6,402,109 B1 * | 6/2002 | Dittmer .................. F16M 11/10 |
| | | 248/480 |

(Continued)

FOREIGN PATENT DOCUMENTS

| CN | 2831695 Y | 10/2006 |
| CN | 201063966 Y | 5/2008 |

(Continued)

*Primary Examiner* — Anthony M Haughton
*Assistant Examiner* — Theron S Milliser
(74) *Attorney, Agent, or Firm* — Westman, Champlin & Koehler, P.A.

(57) ABSTRACT

A shielding cover and a display device are provided. The shielding cover includes: a shielding cover body; and a shielding cover accessory fixedly connected to the shielding cover body. The shielding cover accessory includes: an accessory bottom including a flat bottom; a connecting arm through which the shielding cover accessory is connected to the shielding cover body; and a positioning arm. The connecting arm and the positioning arm are connected to two opposite ends of the accessory bottom, and protrude in opposite directions from the accessory bottom. The shielding cover accessory further includes a plurality of card slots arranged at positions of the flat bottom close to the positioning arm, each card slot penetrates the flat bottom in a direction perpendicular to the flat bottom, and the plurality of card slots are arranged at intervals in a direction parallel to an extending direction of the positioning arm.

20 Claims, 15 Drawing Sheets

(51) Int. Cl.
| | |
|---|---|
| *C07D 209/10* | (2006.01) |
| *C07D 209/30* | (2006.01) |
| *C07D 401/04* | (2006.01) |
| *C07D 403/04* | (2006.01) |
| *C07D 405/04* | (2006.01) |
| *C07D 409/04* | (2006.01) |
| *C07D 417/04* | (2006.01) |
| *C07D 471/04* | (2006.01) |
| *C07D 487/04* | (2006.01) |
| *C07D 498/04* | (2006.01) |
| *G06F 1/18* | (2006.01) |
| *H05K 5/03* | (2006.01) |
| *H05K 9/00* | (2006.01) |

(52) U.S. Cl.
CPC ......... *C07D 209/30* (2013.01); *C07D 401/04* (2013.01); *C07D 403/04* (2013.01); *C07D 405/04* (2013.01); *C07D 409/04* (2013.01); *C07D 417/04* (2013.01); *C07D 471/04* (2013.01); *C07D 487/04* (2013.01); *C07D 498/04* (2013.01); *G06F 1/1656* (2013.01); *G06F 1/182* (2013.01); *H05K 5/03* (2013.01)

(56) References Cited

U.S. PATENT DOCUMENTS

| | | | | |
|---|---|---|---|---|
| 6,680,843 B2 * | 1/2004 | Farrow | .................. | G06F 1/181 |
| | | | | 361/679.02 |
| 7,513,468 B2 * | 4/2009 | Jung | .................... | F16M 11/048 |
| | | | | 248/133 |
| 7,604,206 B2 * | 10/2009 | Jung | .................... | F16M 11/046 |
| | | | | 248/133 |
| 7,819,368 B2 * | 10/2010 | Jung | .................... | F16M 11/048 |
| | | | | 248/133 |
| 8,011,624 B2 * | 9/2011 | Fujikawa | ............... | F16M 11/10 |
| | | | | 248/676 |
| 8,047,487 B2 * | 11/2011 | Hwang | ................ | F16M 11/105 |
| | | | | 248/370 |
| 8,142,064 B2 * | 3/2012 | Baek | .................... | G06F 1/1601 |
| | | | | 348/836 |
| 8,162,675 B2 | 4/2012 | Regnier et al. | | |
| 8,187,019 B2 | 5/2012 | Reed et al. | | |
| 8,218,305 B2 * | 7/2012 | Matsutani | ................ | H05K 7/00 |
| | | | | 361/679.01 |
| 8,226,441 B2 | 7/2012 | Regnier et al. | | |
| 8,241,045 B2 | 8/2012 | Reed et al. | | |
| 8,342,881 B2 | 1/2013 | Lang et al. | | |
| 8,414,324 B2 | 4/2013 | Reed et al. | | |
| 8,439,704 B2 | 5/2013 | Reed | | |
| 8,449,312 B2 | 5/2013 | Lang et al. | | |
| 8,460,033 B2 | 6/2013 | Regnier et al. | | |
| 8,465,302 B2 | 6/2013 | Regnier et al. | | |
| 8,570,721 B2 * | 10/2013 | Tang | .................... | G06F 1/1656 |
| | | | | 345/169 |
| 8,573,997 B2 | 11/2013 | Neer et al. | | |
| 8,597,055 B2 | 12/2013 | Regnier et al. | | |
| 8,599,574 B2 * | 12/2013 | Peng | ................ | G02F 1/133308 |
| | | | | 361/799 |
| 8,678,839 B2 | 3/2014 | Reed et al. | | |
| 8,733,716 B2 * | 5/2014 | Li | ........................ | G06F 1/1601 |
| | | | | 248/188 |
| 8,740,646 B2 | 6/2014 | Lang et al. | | |
| 8,753,145 B2 | 6/2014 | Lang et al. | | |
| 8,821,168 B2 | 9/2014 | Reed et al. | | |
| 9,042,092 B2 * | 5/2015 | Lu | ........................ | F16M 11/041 |
| | | | | 361/679.29 |
| 9,461,392 B2 | 10/2016 | Regnier et al. | | |
| 9,748,713 B2 | 8/2017 | Regnier et al. | | |
| 2002/0130981 A1 * | 9/2002 | Ma | ........................ | F16M 11/10 |
| | | | | 348/843 |
| 2003/0063432 A1 * | 4/2003 | Farrow | .................. | G06F 1/1601 |
| | | | | 361/679.02 |
| 2003/0132360 A1 | 7/2003 | Ju | | |
| 2004/0056161 A1 * | 3/2004 | Ishizaki | ................ | F16C 11/106 |
| | | | | 248/917 |
| 2004/0211866 A1 * | 10/2004 | Jung | .................... | F16M 13/02 |
| | | | | 248/921 |
| 2005/0006537 A1 * | 1/2005 | Jung | .................... | F16M 11/048 |
| | | | | 248/133 |
| 2005/0017135 A1 * | 1/2005 | Jung | .................... | F16M 11/10 |
| | | | | 248/133 |
| 2005/0258334 A1 * | 11/2005 | Hwang | ................ | F16M 11/105 |
| | | | | 248/920 |
| 2006/0076463 A1 * | 4/2006 | Drew | .................... | G06F 1/1601 |
| | | | | 248/917 |
| 2008/0239645 A1 | 10/2008 | Li | | |
| 2009/0154076 A1 * | 6/2009 | Beak | .................... | F16M 11/105 |
| | | | | 361/679.01 |
| 2011/0212633 A1 | 9/2011 | Regnier et al. | | |
| 2011/0212643 A1 | 9/2011 | Reed et al. | | |
| 2011/0223805 A1 | 9/2011 | Regnier et al. | | |
| 2011/0223809 A1 | 9/2011 | Reed et al. | | |
| 2011/0223810 A1 | 9/2011 | Regnier et al. | | |
| 2011/0230104 A1 | 9/2011 | Lang et al. | | |
| 2011/0256776 A1 | 10/2011 | Reed | | |
| 2011/0269338 A1 | 11/2011 | Lang et al. | | |
| 2011/0294347 A1 | 12/2011 | Lang et al. | | |
| 2012/0214327 A1 | 8/2012 | Reed et al. | | |
| 2012/0224329 A1 * | 9/2012 | Li | ........................ | G06F 1/1656 |
| | | | | 361/720 |
| 2012/0236446 A1 * | 9/2012 | Peng | ................ | G02F 1/133308 |
| | | | | 361/679.01 |
| 2012/0250232 A1 * | 10/2012 | Li | ........................ | F16M 11/041 |
| | | | | 361/679.01 |
| 2012/0264325 A1 | 10/2012 | Reed et al. | | |
| 2012/0327570 A1 * | 12/2012 | Tang | .................... | G06F 1/1616 |
| | | | | 361/679.01 |
| 2013/0005173 A1 | 1/2013 | Reed et al. | | |
| 2013/0072062 A1 | 3/2013 | Regnier et al. | | |
| 2013/0157512 A1 | 6/2013 | Regnier et al. | | |
| 2013/0189876 A1 | 7/2013 | Lang et al. | | |
| 2014/0170887 A1 | 6/2014 | Reed et al. | | |
| 2014/0335736 A1 | 11/2014 | Regnier et al. | | |
| 2017/0018894 A1 | 1/2017 | Regnier et al. | | |
| 2018/0263143 A1 | 9/2018 | Chang et al. | | |

FOREIGN PATENT DOCUMENTS

| | | |
|---|---|---|
| CN | 101276651 A | 10/2008 |
| CN | 201383290 Y | 1/2010 |
| CN | 201562834 U | 8/2010 |
| CN | 202171705 U | 3/2012 |
| CN | 203812505 U | 9/2014 |
| CN | 206923233 U | 1/2018 |
| CN | 208480212 U | 2/2019 |
| CN | 109828638 A | 5/2019 |
| CN | 209710547 U | 11/2019 |

* cited by examiner

SHIELDING COVER AND DISPLAY DEVICE

CROSS REFERENCE TO RELATED APPLICATIONS

This application is a Section 371 National Stage Application of International Application No. PCT/CN2021/093316, filed on May 12, 2021, which published on WO 2022/001389 A1, on Jan. 6, 2022, in Chinese, entitled "SHIELDING COVER AND DISPLAY DEVICE", which claims priority to Chinese Application No. 202010606789.0, filed on Jun. 29, 2020, the disclosures of which is incorporated herein by reference in their entireties.

TECHNICAL FIELD

The present disclosure relates to a field of display technology, and in particular, to a shielding cover and a display device including the shielding cover.

BACKGROUND

Electromagnetic waves generated in an electronic or electrical apparatus may interfere with a signal processing system such as a circuit and a signal line within the apparatus, resulting in malfunction and performance degradation of the apparatus. In addition, excessive electromagnetic waves may cause harm to human health. Therefore, in an electronic or electrical apparatus such as a display device, a shielding cover is generally used to isolate or reduce the electromagnetic wave generated by the apparatus during operation, so that the apparatus meets industry standards for electromagnetic radiation.

SUMMARY

In order to solve at least one aspect of the above problems, the embodiments of the present disclosure provide a shielding cover and a display device including the shielding cover.

In one aspect, a shielding cover is provided, including:
a shielding cover body; and
a shielding cover accessory, wherein the shielding cover accessory is fixedly connected to the shielding cover body, and the shielding cover accessory includes:
an accessory bottom including a flat bottom;
a connecting arm, wherein the shielding cover accessory is connected to the shielding cover body through the connecting arm; and
a positioning arm, wherein the connecting arm and the positioning arm are connected to two opposite ends of the accessory bottom, and the connecting arm and the positioning arm are configured to protrude in opposite directions from the accessory bottom,
wherein the shielding cover accessory further includes a plurality of card slots, the plurality of card slots are arranged at positions of the flat bottom close to the positioning arm, each card slot is configured to penetrate the flat bottom in a direction perpendicular to the flat bottom, and the plurality of card slots are arranged at intervals in a direction parallel to an extending direction of the positioning arm.

According to some exemplary embodiments, a shape of an orthographic projection of each card slot on the flat bottom has a rectangular shape, each card slot has a first size in a direction parallel to the extending direction of the positioning arm and a second size in a direction perpendicular to the extending direction of the positioning arm, and the first size is greater than the second size.

According to some exemplary embodiments, the shielding cover accessory further includes a plurality of first openings arranged on the flat bottom, each first opening is configured to penetrate the flat bottom in the direction perpendicular to the flat bottom, and the plurality of first openings are arranged at intervals in the direction parallel to the extending direction of the positioning arm.

According to some exemplary embodiments, the plurality of first openings are respectively arranged adjacent to the plurality of card slots, and a spacing distance among the plurality of first openings in the direction parallel to the extending direction of the positioning arm is greater than a spacing distance among the plurality of card slots in the direction parallel to the extending direction of the positioning arm.

According to some exemplary embodiments, the shielding cover accessory further includes a plurality of first limiting portions, each first limiting portion and the connecting arm are configured to protrude in a same direction relative to the flat bottom, and the plurality of first limiting portions are respectively arranged at the plurality of first openings.

According to some exemplary embodiments, each first limiting portion includes a first limiting sidewall and a first limiting bottom wall, the first limiting sidewall is perpendicular to the flat bottom, and the first limiting bottom wall is parallel to the flat bottom;
the first opening has a first opening sidewall away from the card slot adjacent to the first opening, and the first limiting sidewall is connected to the first opening sidewall; and
the first limiting bottom wall is connected to the first limiting sidewall, and the first limiting bottom wall is configured to extend toward the card slot adjacent to the first limiting bottom wall.

According to some exemplary embodiments, the shielding cover accessory further includes a plurality of second openings, and the plurality of second openings are respectively arranged in the plurality of recesses.

According to some exemplary embodiments, the shielding cover accessory further includes a plurality of second limiting portions, the plurality of second limiting portions and the plurality of first limiting portions are configured to protrude in the same direction relative to the flat bottom, and the plurality of second limiting portions are respectively arranged at the plurality of second openings.

According to some exemplary embodiments, each second limiting portion includes a second limiting sidewall and a second limiting bottom wall, the second limiting sidewall is perpendicular to the flat bottom, and the second limiting bottom wall is parallel to the flat bottom;
the second opening has a second opening sidewall close to a center of the shielding cover accessory, and the second limiting sidewall is connected to the second opening sidewall; and
the second limiting bottom wall is connected to the second limiting sidewall, and the second limiting bottom wall is configured to extend toward the center of the shielding cover accessory.

According to some exemplary embodiments, the shielding cover accessory includes a plurality of first connecting holes, the plurality of first connecting holes are arranged on the connecting arm, and the plurality of first connecting holes are arranged at intervals in the direction parallel to the extending direction of the connecting arm.

According to some exemplary embodiments, the shielding cover accessory further includes a plurality of limiting holes, the plurality of limiting holes are arranged on the connecting arm, and each limiting hole is located between two adjacent first connecting holes.

In another aspect, a display device is provided, including:
the shielding cover described above; and
a rear cover connected to the shielding cover.

According to some exemplary embodiments, the rear cover includes a plurality of hook structures, and the plurality of hook structures are respectively matched with the plurality of card slots of the shielding cover.

According to some exemplary embodiments, the rear cover includes:
a first concave portion configured to receive the shielding cover body;
a second concave portion configured to receive the shielding cover accessory; and
a positioning bottom and a connecting sidewall arranged in the second concave portion;
wherein the first concave portion has a first concave bottom and four concave sidewalls, the second concave portion has a second concave bottom, a first concave sidewall, a second concave sidewall, a third concave sidewall and a concave opening, the first concave sidewall is opposite to the concave opening, the second concave sidewall is opposite to the third concave sidewall, and the first concave portion is communicated with the second concave portion through the concave opening; and
the positioning bottom has a flat surface, a side of the positioning bottom is connected to the second concave bottom through the connecting sidewall, and the other side of the positioning bottom is connected to the first concave sidewall.

According to some exemplary embodiments, each hook structure includes:
a body portion, wherein the body portion is configured to protrude toward the shielding cover relative to the positioning bottom; and
a hook portion, wherein an end of the hook portion is connected to the body portion, and the hook portion is configured to protrude in a direction toward the first concave sidewall relative to the body portion.

According to some exemplary embodiments, the hook portion is spaced from the positioning bottom by a first distance in a direction perpendicular to the positioning bottom, and the first distance is greater than a thickness of the flat bottom of the shielding cover in a direction perpendicular to the positioning bottom.

According to some exemplary embodiments, the hook portion has a chamfered portion, the chamfered portion is arranged at an edge of the hook portion facing the first concave sidewall and the positioning bottom.

According to some exemplary embodiments, each hook structure further includes a reinforcing rib arranged on a side of the body portion away from the hook portion.

According to some exemplary embodiments, an area of an orthographic projection of each hook structure on the positioning bottom is smaller than an area of an orthographic projection of each card slot on the positioning bottom.

According to some exemplary embodiments, the flat bottom of the shielding cover accessory is abutted against the positioning bottom of the rear cover.

According to some exemplary embodiments, the accessory bottom of the shielding cover accessory further includes a plurality of recesses, the plurality of recesses and the connecting arm are configured to protrude in the same direction relative to the flat bottom, and the plurality of recesses are arranged at intervals in the direction parallel to the extending direction of the positioning arm; and
the rear cover further includes a plurality of receiving portions, the plurality of receiving portions are respectively located on two sides of the positioning bottom, and the plurality of receiving portions are configured to respectively receive the plurality of recesses of the shielding cover accessory.

According to some exemplary embodiments, the rear cover further includes a first set of supporting ribs located between the second concave sidewall and one of the receiving portions, and a second set of supporting ribs located between the third concave sidewall and another one of the receiving portions, and each of the first set of supporting ribs and the second set of supporting ribs includes a plurality of supporting ribs.

According to some exemplary embodiments, the display device further includes a base including a bracket, and a part of the bracket is positioned between the shielding cover accessory and the rear cover.

According to some exemplary embodiments, the shielding cover accessory includes a plurality of first limiting portions and a plurality of second limiting portions, and each of the plurality of first limit portions and the plurality of second limit portions includes a limiting sidewall and a limiting bottom wall,
a part of the bracket is positioned between the positioning bottom of the rear cover and the limiting bottom wall, so as to limit a movement of the bracket in the direction perpendicular to the positioning bottom, and According to some exemplary embodiments, a part of the bracket is further positioned between the limiting sidewalls of the plurality of first limiting portions and between the limiting sidewalls of the plurality of second limiting portions, so as to limit a movement of the bracket in a direction perpendicular to the limiting sidewall.

BRIEF DESCRIPTION OF THE DRAWINGS

Through following descriptions of the present disclosure with reference to drawings, other purposes and advantages of the present disclosure will become apparent and a comprehensive understanding of the present disclosure may be obtained.

Figure 1:
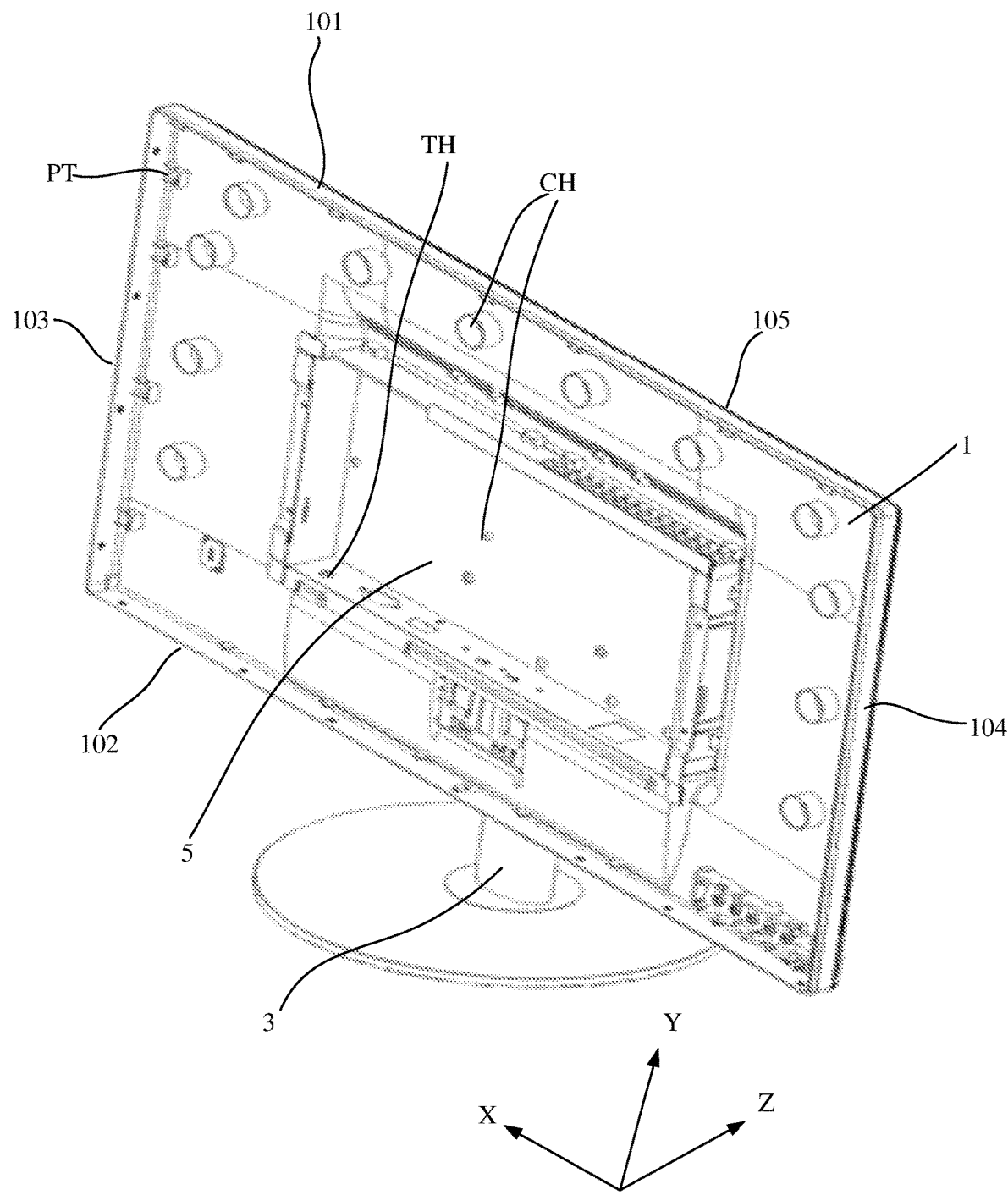
FIG. 1 is a schematic perspective view of a display device according to the embodiments of the present disclosure.

It should be noted that, for clarity, sizes of layers, structures, or regions may be enlarged or reduced in the drawings of the embodiments of the present disclosure, that is, the drawings are not drawn according to actual scale.

DETAILED DESCRIPTION OF EMBODIMENTS

In order to make purposes, technical solutions and advantages of the embodiments of the present disclosure more apparent, the technical solutions in the embodiments of the present disclosure will be clearly and completely described in conjunction with the drawings in the embodiments of the present disclosure. Obviously, the described embodiments are merely a part of the embodiments of the present disclosure, rather than all the embodiments. Based on the described embodiments of the present disclosure, all other embodiments obtained by those skilled in the art without creative work are within the protection scope of the present disclosure.

Unless otherwise defined, technical or scientific terms used in the present disclosure should have general meanings understood by those skilled in the art. "First" "second" and similar terms used in the present disclosure do not denote any order, quantity, or importance, but are merely used to distinguish different components. "Comprise" or "include" and similar terms mean that the elements or items appearing before the term encompass elements, items and their equivalents listed after the term, but do not exclude other elements or items.

In the present disclosure, unless otherwise specified, directional terms such as "upper," "lower," "left," "right," "inner," "outer," and the like are used to denote an orientation or a positional relationship based on the drawings, which is for ease of describing the present disclosure only, and is not intended to indicate or imply the related device, element or component must have a particular orientation, be constructed or operated in a particular orientation. It should be understood that, when absolute positions of the described objects are changed, a relative positional relationship thereof may also be changed accordingly. Therefore, these directional terms should not be construed as limiting the present disclosure.

Figure 2:
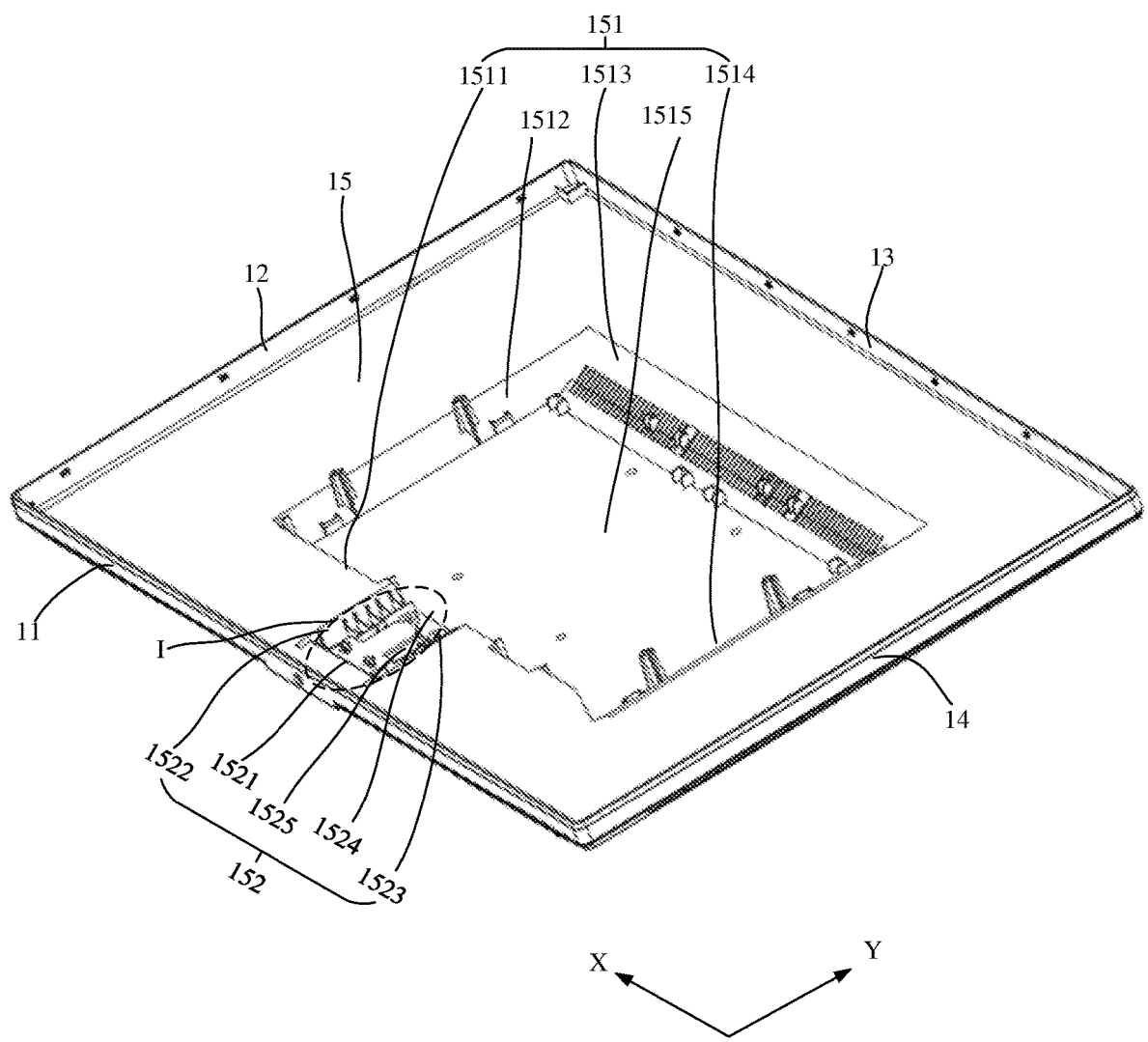
FIG. 2 is a schematic perspective view of a rear cover included in a display device according to some exemplary embodiments of the present disclosure.

FIG. 1 is a schematic perspective view of a display device according to the embodiments of the present disclosure. It should be noted that, in the present disclosure, for ease of description, a XYZ space coordinate system is established. Referring to FIGS. 1 and 2, a display device 100 includes 4 frames, that is, a first frame 101 on an upper side (also referred to as a sky side) of FIG. 1, a second frame 102 on a lower side (also referred to as a ground side) of FIG. 1, a third frame 103 on a left side of FIG. 1, and a fourth frame 104 on a right side of FIG. 1.

In FIG. 1, a back surface of the display device 100 is located on a side of the paper surface facing outward, and a display surface of the display device 100 is located on a side of the paper surface facing inward. It should be understood that the display device 100 may include the display surface 105 and the back surface. The display surface 105 is used to display text, images and other information for users to view. The back surface is located on a side of the display device 100 opposite to the display surface 105. For ease of description, a side where the display surface 105 of the display device 100 is located is referred to as a display side, and a side where the back surface of the display device 100 is located is referred to as a back side.

For example, in the embodiment shown in FIG. 1, a X direction may be a direction parallel to the first frame 101 or the second frame 102, a Y direction may be a direction parallel to the third frame 103 or the fourth frame 104, and a Z direction may be a direction perpendicular to the display surface 105, that is, the Z direction is a thickness direction of the display device 100. It should also be noted that, in the present disclosure, the X direction may also be referred to as a first direction, the Y direction may also be referred to as a second direction, and the Z direction may also be referred to as a third direction. It should be noted that expressions of the XYZ space coordinate system, the X direction, the Y direction and the Z direction are only for ease of describing the embodiments of the present disclosure, and should not be construed as limiting the present disclosure.

Continuing to refer to FIG. 1, the display device 100 may include a rear cover 1, a base 3 and a shielding cover 5. For example, the display device 100 may include components such as a display panel, a front cover, a main circuit board, the shielding cover 5, the rear cover 1, the base 3, etc. The rear cover 1 is located on the back side of the display device 100, and the shielding cover 5 may be located between the main circuit board and the rear cover 1. A plug of the display device sequentially passes through the rear cover 1 and the shielding cover 5, and is inserted into an input/output interface on the main circuit board, so as to achieve signal transmission between the display device and an external apparatus. The base 3 is located on the lower side of the display device 100 and is used to support an assembly composed of components such as the display panel, the rear cover 1, the shielding cover 5, etc.

Structures of the components such as the rear cover 1, the base 3, the shielding cover 5, etc. included in the display device 100 will be described in detail below with reference to the drawings. It should be noted that, as shown in FIG. 1, the display device 100 may further include a connecting hole CH, a through hole TH, a positioning structure PT and other structures provided on the rear cover 1. In the following illustrations or descriptions, in order to highlight structures related to the inventive concept of the present disclosure, these structures may be omitted.

FIG. 2 is a schematic perspective view of the rear cover included in the display device according to some exemplary embodiments of the present disclosure. Referring to FIG. 2, the rear cover 1 includes a rear cover board 15 and four side boards 11, 12, 13 and 14. The four side boards 11, 12, 13 and 14 respectively extend from the rear cover board 15 toward the back side of the display device 100, and the four side boards 11, 12, 13 and 14 are substantially perpendicular to the rear cover board 15, respectively. The four side panels are connected end to end to form a surrounding structure. The rear cover board 15 has a first concave portion 151 and a second concave portion 152. The first concave portion 151 is closer to the display side of the display device 100 than the second concave portion 152. That is, a depth of the first concave portion 151 is greater than a depth of the second concave portion 152.

The first concave portion 151 has a first concave bottom 1515 and four concave sidewalls 1511, 1512, 1513 and 1514. The four concave sidewalls 1511, 1512, 1513 and 1514 extend from the first concave bottom 1515 toward the back side of the display device 100, respectively, and the four concave sidewalls 1511, 1512, 1513 and 1514 are substantially perpendicular to the first concave bottom 1515, respectively. The four concave sidewalls are connected end to end to form a surrounding structure. In this way, the first concave bottom 1515 and the four concave sidewalls 1511, 1512, 1513 and 1514 surround to form a first accommodating space. It should be understood that electronic elements such as a main circuit board, etc. are provided at a position corresponding to the first accommodating space.

The second concave portion 152 has a second concave bottom 1525, three concave sidewalls 1521, 1522 and 1523, and a concave opening 1524. For ease of description, the three concave sidewalls 1521, 1522 and 1523 are referred to as a first concave sidewall 1521, a second concave sidewall 1522 and a third concave sidewall 1523, respectively.

The concave opening 1524 is formed on the concave sidewall 1511 of the first concave portion 151. The first concave sidewall 1521 is opposite to the concave opening 1524, and the second concave sidewall 1522 and the third concave sidewall 1523 are opposite to each other. In this way, the second concave bottom 1525 and the three concave sidewalls 1521, 1522, 1523 surround to form a second accommodating space. The second accommodating space has an opening 1524. The first accommodating space is communicated with the second accommodating space through the concave opening 1524.

Figure 3:
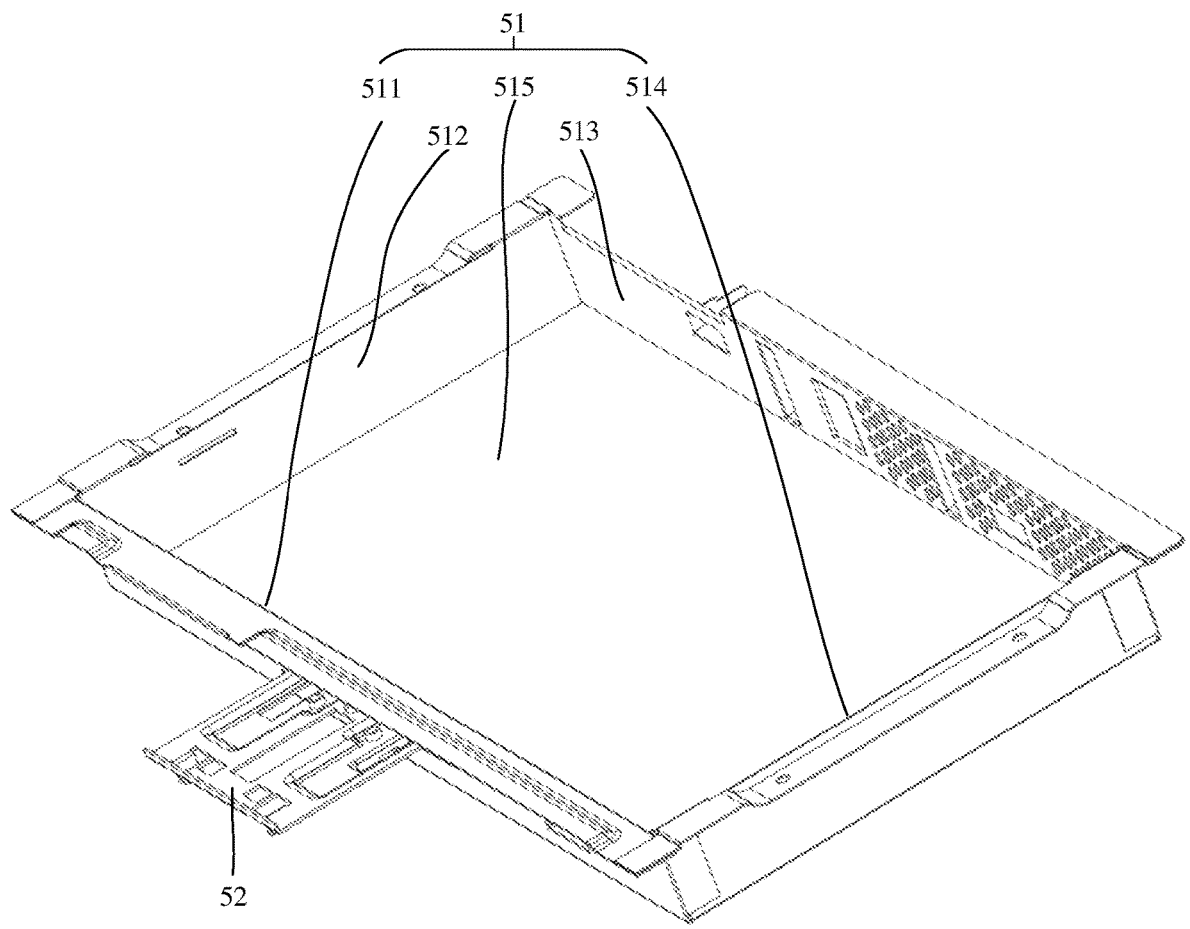
FIG. 3 is a schematic perspective view of a shielding cover included in a display device according to some exemplary embodiments of the present disclosure.
Figure 4:
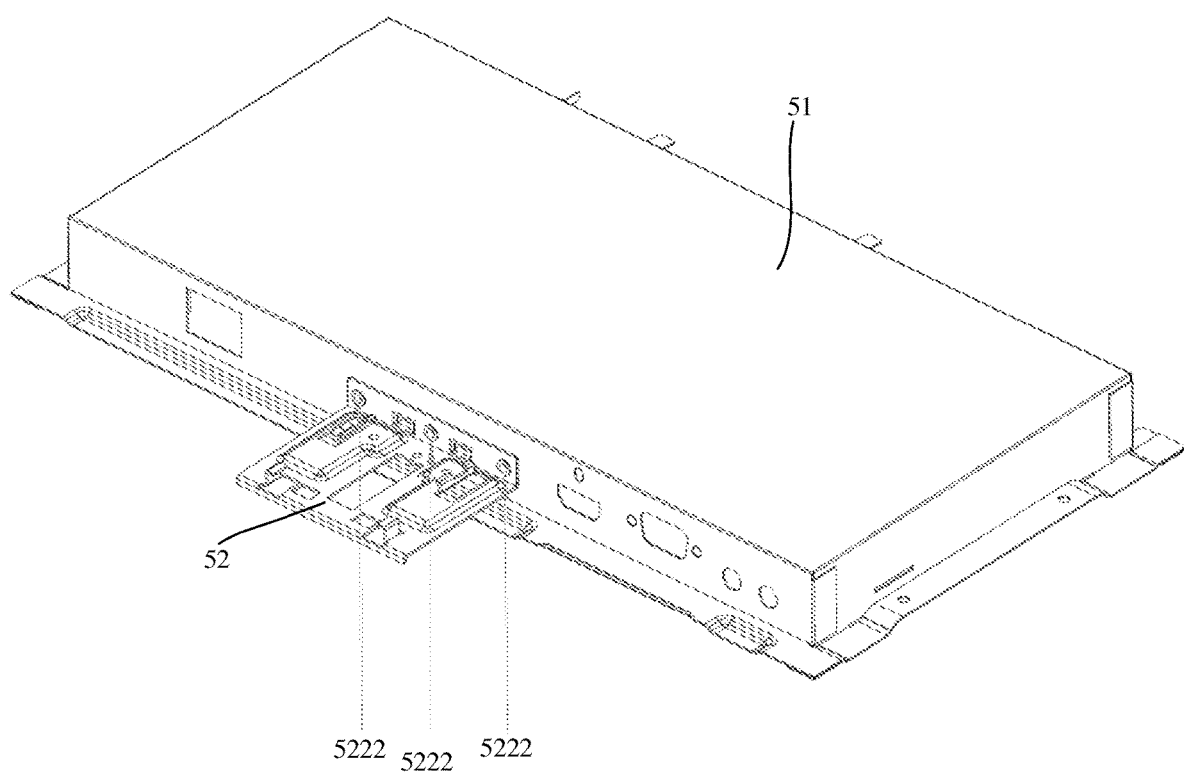
FIG. 4 is a schematic perspective view of the shielding cover shown in FIG. 3 viewed from another perspective (eg, viewed from a back surface)

FIG. 3 is a schematic perspective view of the shielding cover included in the display device according to some exemplary embodiments of the present disclosure, and FIG. 4 is a schematic perspective view of the shielding cover shown in FIG. 3 viewed from another perspective (eg, viewed from the back surface). Referring to FIG. 3 and FIG. 4, the shielding cover 5 includes a shielding cover body 51 and a shielding cover accessory 52.

It should be noted that, in the present disclosure, the expression "shielding cover accessory" may refer to a part of the shielding cover connected with a bracket. For example, the shielding cover accessory may be a separate sheet metal part which is fixedly connected to the shielding cover body through a fixing element.

The shielding cover body 51 includes a shielding cover body bottom 515 and four shielding cover sidewalls 511, 512, 513 and 514. The four shielding cover sidewalls 511, 512, 513 and 514 extend from the shielding cover body bottom 515 toward the back side of the display device 100, respectively, and the four shielding cover sidewalls 511, 512, 513 and 514 are substantially perpendicular to the shielding cover body bottom 515, respectively. The four shielding cover sidewalls are connected end to end to form a surrounding structure.

For ease of description, the four shielding cover sidewalls 511, 512, 513 and 514 are respectively referred to as a first shielding cover sidewall 511, a second shielding cover sidewall 512, a third shielding cover sidewall 513 and a fourth shielding cover sidewall 514. The first shielding cover sidewall 511 is opposite to the third shielding cover sidewall 513, and the second shielding cover sidewall 512 is opposite to the fourth shielding cover sidewall 514.

Figure 5:
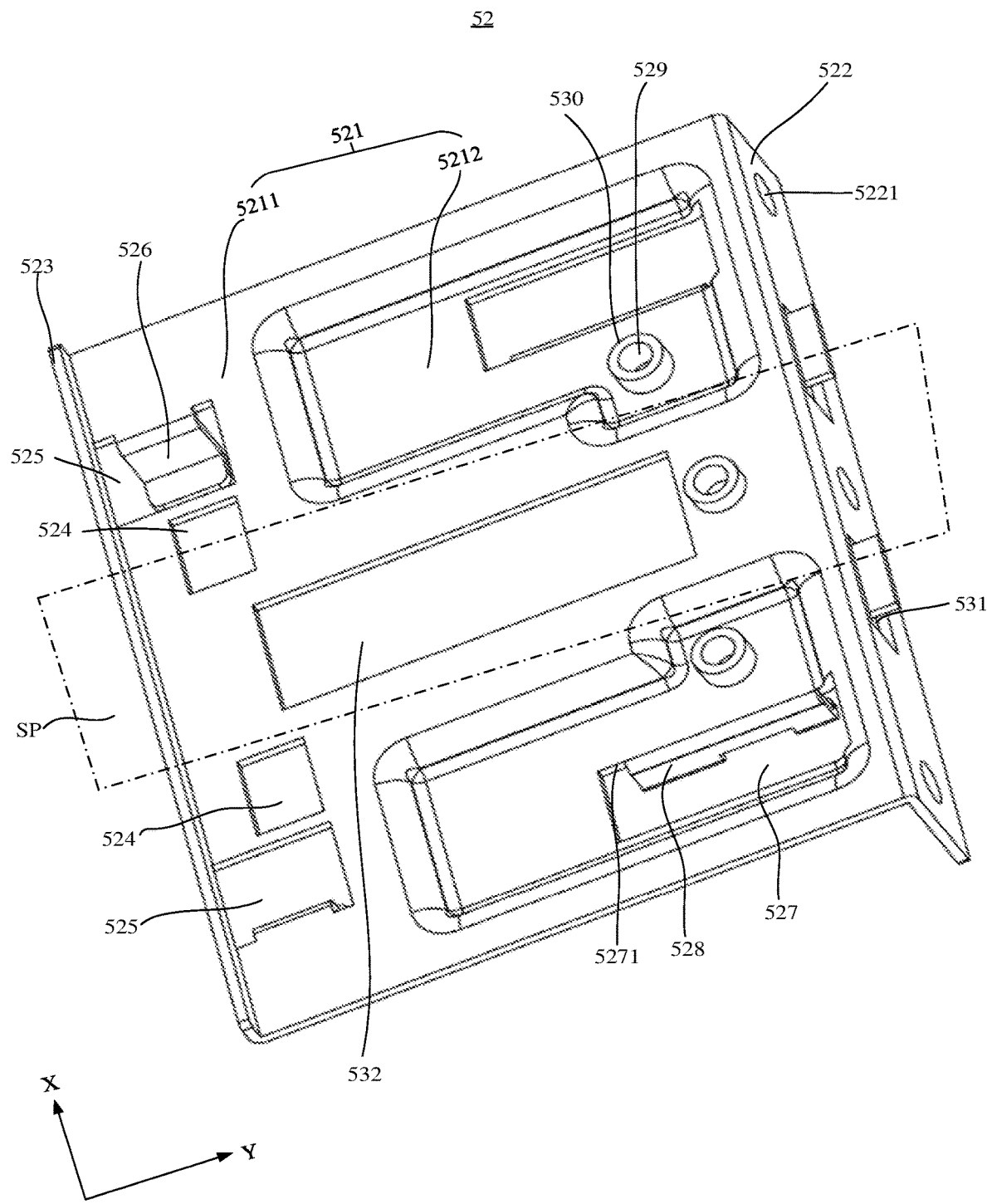
FIG. 5 is a schematic perspective view of a shielding cover accessory included in a shielding cover according to some exemplary embodiments of the present disclosure.
Figure 6:
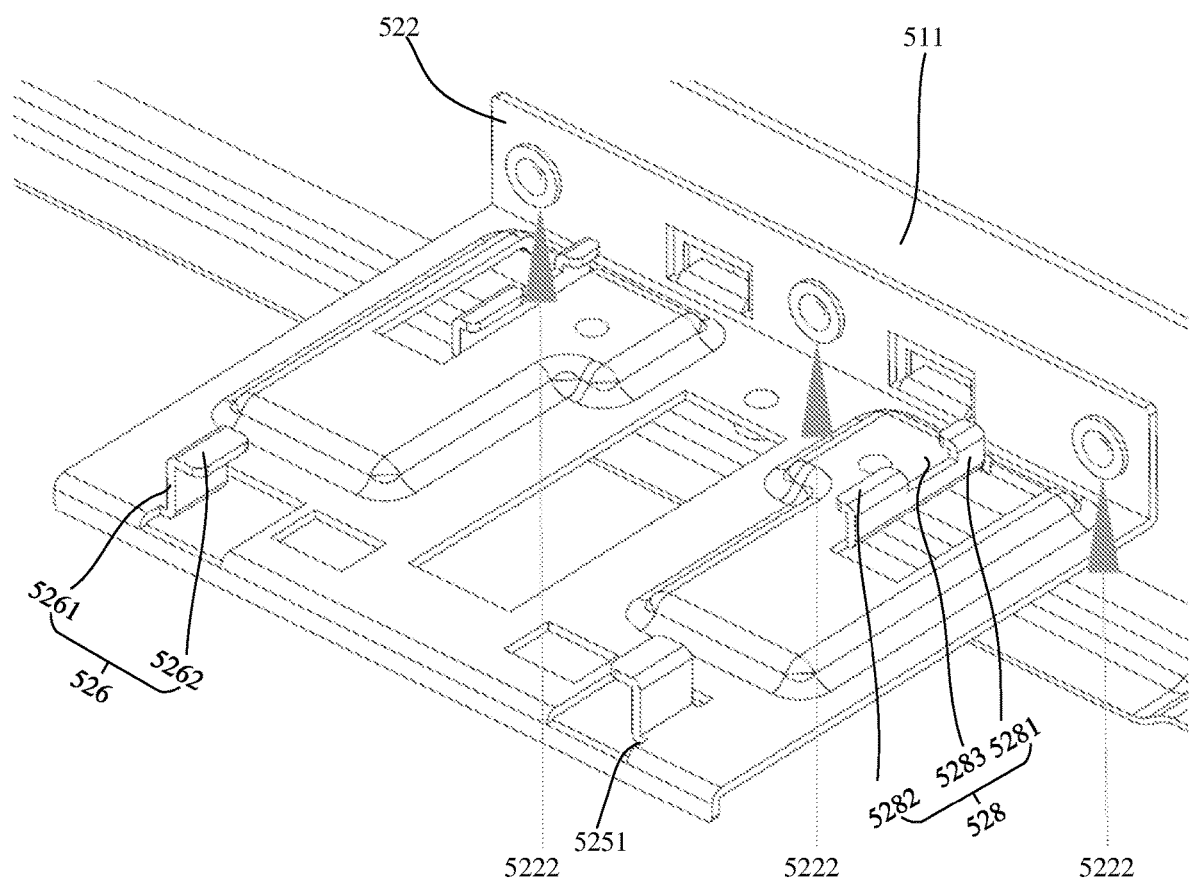
FIG. 6 is a schematic perspective view of a shielding cover accessory included in a shielding cover according to some exemplary embodiments of the present disclosure viewed from another perspective (eg, viewed from a back surface)

FIG. 5 is a schematic perspective view of the shielding cover accessory included in the shielding cover according to some exemplary embodiments of the present disclosure. FIG. 6 is a schematic perspective view of the shielding cover accessory included in the shielding cover according to some exemplary embodiments of the present disclosure viewed from another perspective (eg, viewed from its back surface).

Referring to FIGS. 3 to 6, the shielding cover accessory 52 includes an accessory bottom 521, a connecting arm 522 and a positioning arm 523. The connecting arm 522 and the positioning arm 523 are connected to two opposite ends of the accessory bottom 521, and extend from the accessory bottom 521 toward opposite directions. For example, the connecting arm 522 extends from the accessory bottom 521 toward the back side, and the positioning arm 523 extends from the accessory bottom 521 toward the display side.

The connecting arm 522 is fixedly connected to the first shielding cover sidewall 511 through a connecting piece. For example, the connecting piece may include a plurality of rivets 5222, such as 3 rivets. Specifically, the connecting arm 522 is provided with a plurality of (eg, three) first connecting holes 5221, and the plurality of first connecting holes 5221 are distributed at intervals on the connecting arm 522 in the X direction. The plurality of rivets 5222 are inserted into the plurality of first connecting holes 5221, respectively. In this way, the shielding cover accessory 52 is fixedly connected to the shielding cover body 51 by riveting.

The accessory bottom 521 includes a flat bottom 5211 and a plurality of recesses 5212 recessed relative to the flat bottom 5211. For example, the number of the recesses 5212 may be two. The plurality of recesses 5212 protrude toward the back side relative to the flat bottom 5211. That is, the plurality of recesses 5212 and the connecting arm 522 protrude in the same direction relative to the flat bottom 5211. The plurality of recesses 5212 are arranged at intervals in the X direction.

Optionally, the shielding cover accessory 52 may have a symmetrical structure relative to a symmetry plane SP. For example, the symmetry plane SP may be perpendicular to the flat bottom 5211. Each first connecting hole 5221 may have a shape of circular, that is, each first connecting hole 5221 has a center. The symmetry plane SP may pass through a center of a connecting hole 5221 centered in the three first connecting holes 5221.

The shielding cover accessory 52 further includes a plurality of card slots 524 arranged on the accessory bottom 521. For example, the number of the card slots 524 may be two.

The plurality of card slots 524 are arranged at positions of the accessory bottom 521 close to the positioning arm 523. Each card slot 524 penetrates the accessory bottom 521 in the Z direction (ie, the direction perpendicular to the flat bottom 5211). Specifically, each card slot 524 penetrates the flat bottom 5211 in the Z direction, and the plurality of card slots 524 are arranged at intervals in the X direction.

For example, a projection of each card slot 524 in the Z direction (ie, in the XY plane) has a shape of substantially rectangular. Each card slot 524 has a first size L1 in the X direction and a second size W1 in the Y direction, and the first size L1 may be greater than the second size W1.

The shielding cover accessory 52 may further include a plurality of first openings 525 arranged on the accessory bottom 521. For example, the number of the first openings 525 may be two.

The plurality of first openings 525 are arranged at positions of the accessory bottom 521 close to the positioning arms 523. Each first opening 525 penetrates the accessory bottom 521 in the Z direction. Specifically, each first opening 525 penetrates through the flat bottom 5211 in the Z direction, and the plurality of first openings 525 are arranged at intervals in the X direction.

The plurality of first openings 525 correspond to and are located adjacent to the plurality of card slots 524, respectively. Moreover, each first opening 525 is located on a side of the card slot 524 adjacent thereto away from the symmetry plane SP. That is, a spacing distance of the plurality of first openings 525 in the X direction is greater than a spacing distance of the plurality of card slots 524 in the X direction.

The shielding cover accessory 52 may further include a first limiting portion 526. For example, the number of the first limiting portions 526 may be two. The two first limiting portions 526 may be formed as a pair, and the two first limiting portions cooperate to limit an inserted bracket (which will be described in detail below).

The first limiting portion 526 protrudes toward the back side relative to the flat bottom 5211. That is, the first limiting portion 526 and the connecting arm 522 protrude toward the same direction relative to the flat bottom 5211.

Each first limiting portion 526 includes a first limiting sidewall 5261 and a first limiting bottom wall 5262. The first limiting sidewall 5261 substantially extends in a direction perpendicular to the flat bottom 5211. The first limiting sidewall 5261 is connected to the flat bottom 5211. Specifically, the first opening 525 has a first opening sidewall 5251 away from the card slot 524 adjacent thereto, and the first limiting sidewall 5261 is connected to the first opening sidewall 5251. The first limiting bottom wall 5262 substantially extends in a direction parallel to the flat bottom 5211 and extends toward the symmetry plane SP.

The shielding cover accessory 52 may further include a plurality of second openings 527 on the accessory bottom 521. For example, the number of the second openings 527 may be two. The two second openings 527 may be arranged in the two recesses 5212, respectively.

For example, each second opening 527 may be arranged on a side of the corresponding recess 5212 close to the connecting arm 522. Each second opening 527 penetrates the accessory bottom 521 in the Z direction. Specifically, each second opening 527 penetrates a bottom of the corresponding recess 5212 in the Z direction.

The shielding cover accessory 52 may further include a second limiting portion 528. For example, the number of the second limiting portions 528 may be two. The two second limiting portions 528 may be formed as a pair, and the two second limiting portions cooperate to limit an inserted bracket (which will be described in detail below).

The second limiting portion 528 protrudes toward the back side relative to the bottom of the recess 5212. That is, the second limiting portion 528, the first limiting portion 526 and the connecting arm 522 protrude toward the same direction relative to the flat bottom 5211.

Each second limiting portion 528 includes a second limiting sidewall 5281 and a second limiting bottom wall 5282. The second limiting sidewall 5281 substantially extends in a direction perpendicular to the flat bottom 5211. The second limiting sidewall 5281 is connected to the recess 5212. Specifically, the second opening 527 has a second opening sidewall 5271 close to the symmetry plane SP. The second limiting sidewall 5281 is connected to the second opening sidewall 5271.

The second limiting bottom wall 5282 substantially extends in a direction parallel to the flat bottom 5211 and extends toward the symmetry plane SP. Optionally, the second limiting bottom wall 5282 of each second limiting portion 528 has a notch 5283, that is, the second limiting bottom wall 5282 is broken at the notch 5283, thereby forming two parts.

Optionally, the shielding cover accessory 52 may further include a plurality of second connecting holes 529. Specifically, the shielding cover accessory 52 may include a plurality of connecting columns 530, such as three connection columns 530. Two connecting columns 530 are formed in the two recesses 5212, respectively, and a connecting column 530 is formed on a part of the flat bottom 5211 located between the two recesses 5212. Each connecting column 530 protrudes toward the display side relative to a surface on which the connection column is formed, that is, the connection column 530 and the recess 5212 protrude in opposite directions. A second connecting hole 529 is formed in each connection column 530 to accommodate a fixing element such as a screw.

Optionally, the shielding cover accessory 52 may further include a plurality of limiting holes 531, such as two limiting holes 531. The plurality of limiting holes 531 are arranged on the connecting arm 522. Each limiting hole 531 is located between two adjacent first connecting holes 5221.

For example, an orthographic projection of each limiting hole 531 on the connecting arm 522 has a shape of rectangular, and an orthographic projection of each first connecting hole 5221 on the connection arm 522 has a shape of circular.

Optionally, the shielding cover accessory 52 may further include a through hole 532. The through hole 532 may be arranged on the flat bottom 5211, and most of the through hole 532 is formed on the part of the flat bottom 5211 located between the two recesses 5212. For example, an orthographic projection of the through hole 532 on the flat bottom 5211 has a shape of rectangular.

For example, the shielding cover body 51 and the shielding cover accessory 52 included in the shielding cover 5 may be made of the same material. The material of the shielding cover 5 may include a metal material, such as stainless steel, cupronickel and the like.

Figure 7:
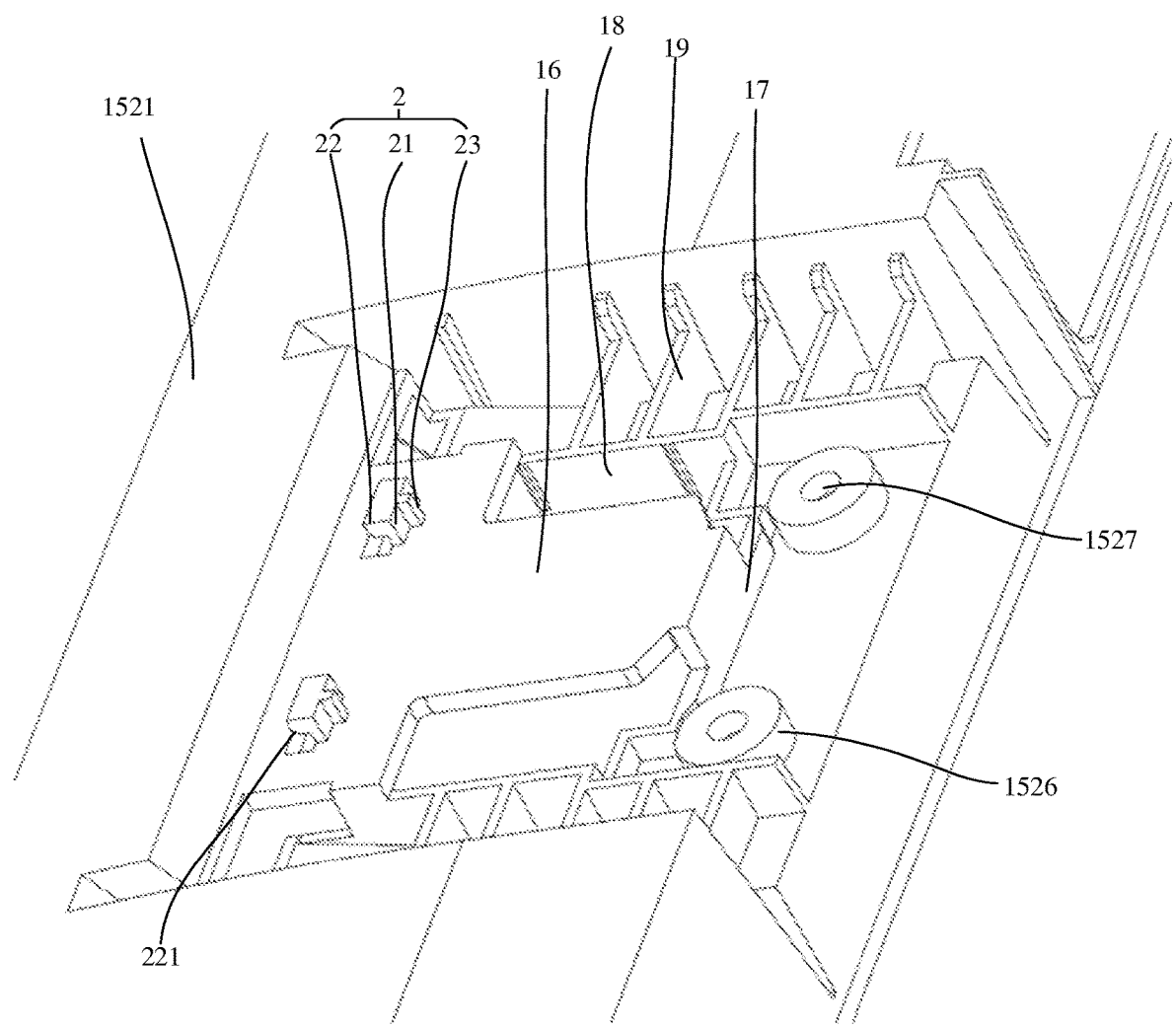
FIG. 7 is a partial enlarged view of part I of the rear cover shown in FIG. 2.

FIG. 7 is a partial enlarged view of part I of the rear cover in FIG. 2. Referring to FIGS. 2 and 7, the rear cover 1 includes a positioning bottom 16 in the second concave portion 152. The positioning bottom 16 has a flat surface. The positioning bottom 16 is substantially parallel to the second concave bottom 1525. Specifically, the rear cover 1 further includes a connecting sidewall 17 in the second concave portion 152, and the connecting sidewall 17 is substantially perpendicular to each of the second concave bottom 1525 and the positioning bottom 16. A side of the positioning bottom 16 is connected to the second concave bottom 1525 through the connecting sidewall 17. The other side of the positioning bottom 16 is connected to the first concave sidewall 1521.

For example, an orthographic projection of the positioning bottom 16 on the second concave bottom 1525 has a shape of substantially T-shaped. Receiving portions 18 are respectively arranged in the narrowed regions of the positioning bottom 16. That is, the rear cover 1 may further include two receiving portions 18 respectively located on two sides of the positioning bottom 16. In this way, when the shielding cover 5 is positioned and connected to the rear cover 1, the two receiving portions 18 are used to respectively receive the two recesses 5212 of the shielding cover accessory 52.

Continuing to refer to FIG. 7, the rear cover 1 further includes a plurality of hook structures 2, such as two hook structures. The two hook structures 2 may be positioned and matched with the two card slots 524 of the shielding cover 5, respectively, so that the shielding cover 5 is positioned and connected to the rear cover 1.

Figure 13:
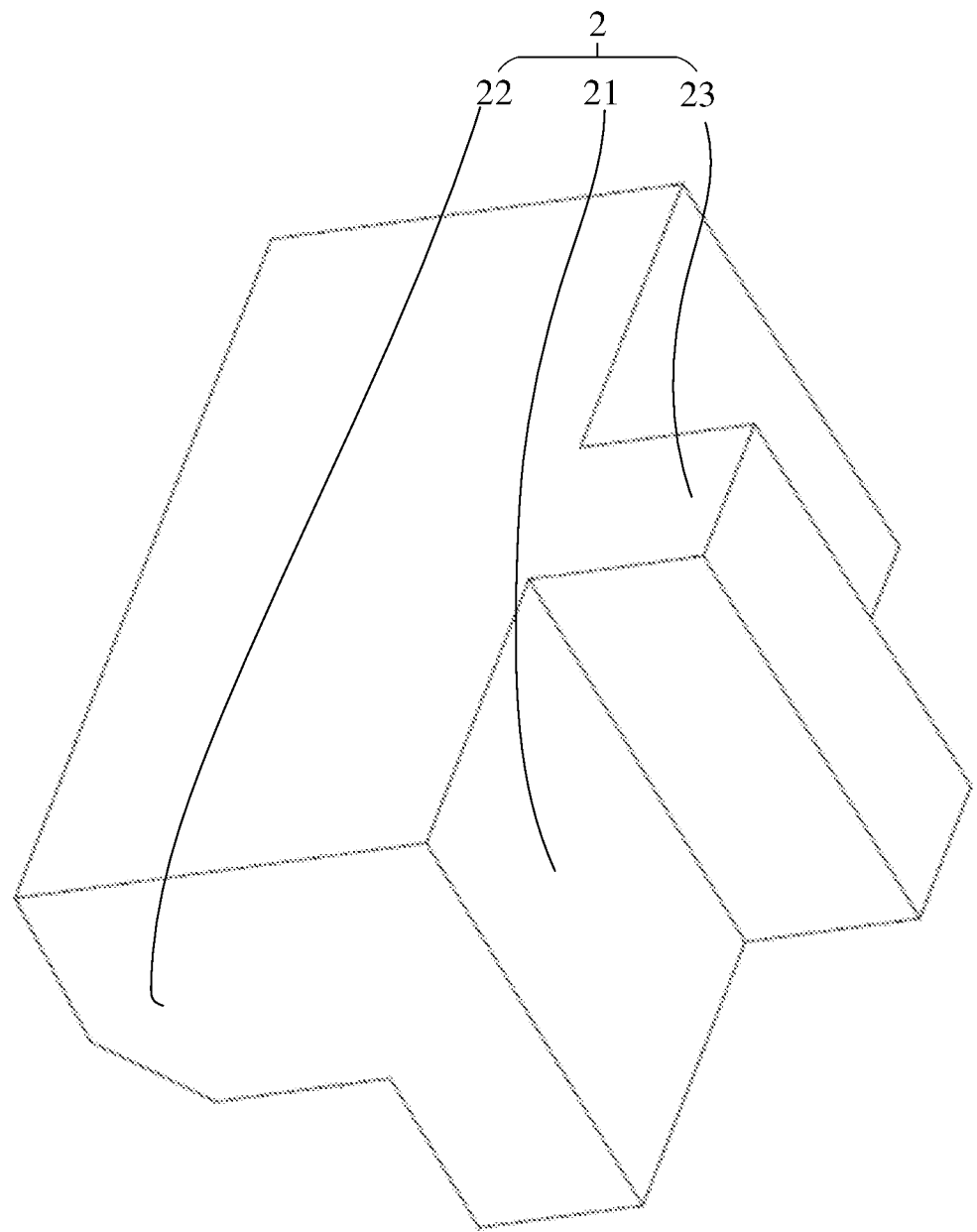
FIG. 13 is a schematic perspective view of a hook structure included in a shielding cover accessory according to some exemplary embodiments of the present disclosure.

Specifically, FIG. 13 is a schematic perspective view of the hook structure included in the shield accessory according to some exemplary embodiments of the present disclosure. With reference to FIGS. 7 and 13, the hook structure 2 may include a body portion 21 and a hook portion 22.

In the Z direction, the body portion 21 protrudes toward the back side of the display device relative to the positioning bottom 16. In the X direction, two body portions 21 are arranged at an interval. In the Y direction, the body portion 21 is adjacent to the first concave sidewall 1521 and is spaced apart from the first concave sidewall 1521 by a certain distance.

An end of the hook portion 22 is connected to the body portion 21 and extends toward the first concave sidewall 1521. That is, the hook portion 22 protrudes toward the first recessed sidewall 1521 relative to the body portion 21. In this way, the hook portion 22 is formed as a cantilever structure, an end of which is connected to the body portion 21. In the Z direction, the hook portion 22 is spaced from the positioning bottom 16 by a certain distance. For example, the distance is greater than a thickness of the flat bottom 5211 of the shielding cover 5, so that a part of the shielding cover accessory 52 may be inserted between the hook portion 22 and the positioning bottom 16.

A size of the hook portion 22 in the Y direction is larger than a size of the body portion 21 in the Y direction. In this way, an orthographic projection of a combination of the hook portion 22 and the body portion 21 in the YZ plane has a shape of inverted L.

The hook portion 22 has a chamfered portion 221. The chamfered portion 221 is arranged at an edge facing the first concave sidewall 1521 and the positioning bottom 16. By arranging such chamfered portion 221, it is conductive to guide the shielding cover accessory 52 to be inserted between the hook portion 22 and the positioning bottom 16.

For example, an orthographic projection of each hook portion 22 on the positioning bottom 16 (ie, an orthographic projection in the Z direction or in the XY plane) has a shape of substantially rectangular. Each hook portion 22 has a first size L2 in the X direction and a second size W2 in the Y direction, and the first size L2 may be greater than the second size W2.

For example, for the hook portion 22 and the card slot 524, the first size L1 of the card slot 524 may be greater than the first size L2 of the hook portion 22, and the second size W1 of the card slot 524 may be greater than the second size W2 of the hook portion 22. In this way, when the shielding cover 5 is positioned and connected to the rear cover 1, the hook portion 22 may be inserted into the card slot 524, so as to achieve the positioning and connection between the shielding cover 5 and the rear cover 1.

Optionally, the hook structure 2 may further include a reinforcing rib 23. The reinforcing rib 23 is arranged on a side of the body portion 21 away from the hook portion 22, and an end of the reinforcing rib 23 is connected to a sidewall of the body portion 21. In the X direction, a size of the reinforcing rib 23 is smaller than the size of the body portion 21. In the Z direction, a size of the reinforcing rib 23 is equal to a size of a combination of the hook portion 22 and the body portion 21, that is, a top surface of the reinforcing rib 23 away from the positioning bottom 16 is flush with a top surface of the hook portion 22 away from the positioning bottom 16. By arranging the reinforcing rib 23, a strength of the hook structure 2 may be increased, so that a matching between the hook structure 2 and the slot 524 may be more firm.

For example, the body portion 21, the hook portion 22 and the reinforcing rib 23 included in the hook structure 2 may be integrally formed.

Optionally, the rear cover 1 may further include a first set of supporting ribs between the second concave sidewall 1522 and a receiving portion 18 and a second set of supporting ribs between the third concave sidewall 1523 and the other receiving portion 18. For example, each of the first set of supporting ribs and the second set of supporting ribs may include a plurality of supporting ribs 19. The plurality of supporting ribs 19 are arranged at intervals in the Y direction.

Optionally, the rear cover 1 may further include a plurality of third connecting holes 1527. Specifically, the rear cover 1 may include a plurality of connecting columns 1526, such as two connecting columns 1526. The two connecting columns 1526 are formed on a part of the second concave bottom 1525 close to the concave opening 1524, and the two connecting columns 1526 are arranged at an interval in the X direction. Each connecting column 1526 protrudes toward the display side relative to the second concave bottom 1525. A third connecting hole 1527 is formed in each connecting column 1526 to accommodate a fixing element such as a screw.

For example, the rear cover 1 may be integrally formed of a material such as plastic.

Figure 8:
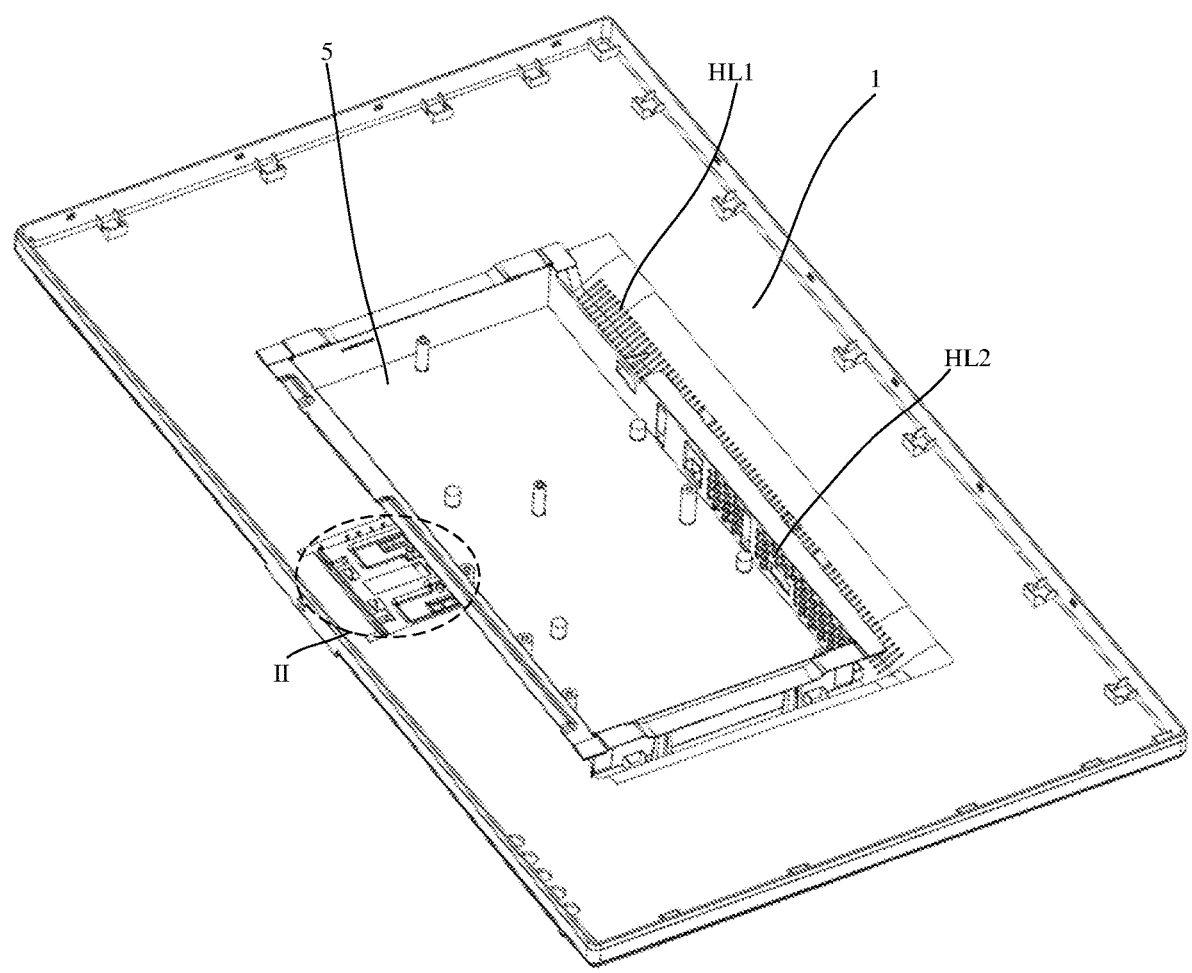
FIG. 8 is a schematic perspective view of a shielding cover and a rear cover in an assembled state according to some exemplary embodiments of the present disclosure.
Figure 9:
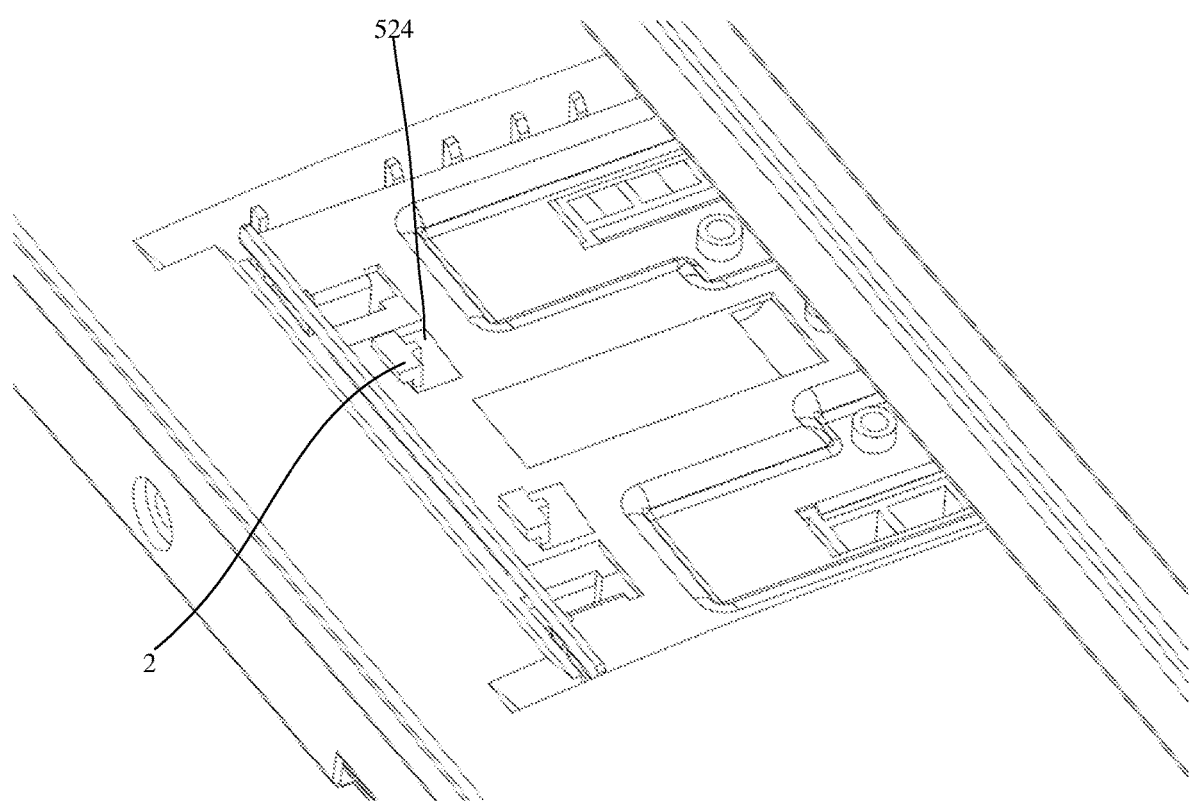
FIG. 9 is a partial enlarged view of part II in FIG. 8.
Figure 14:
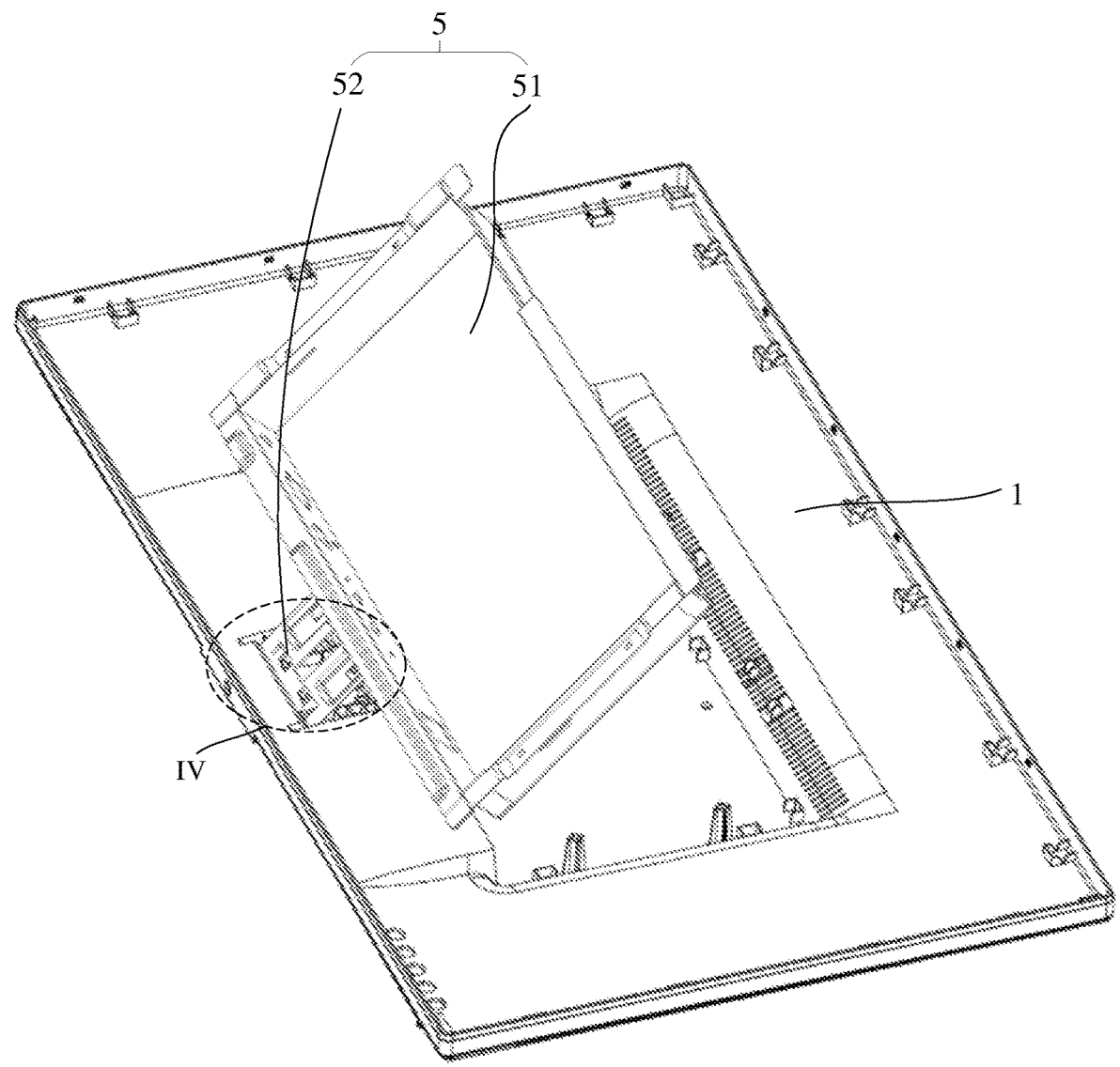
FIG. 14 is a combined schematic view of a shielding cover and a rear cover prior to flipping according to some exemplary embodiments of the present disclosure.
Figure 15:
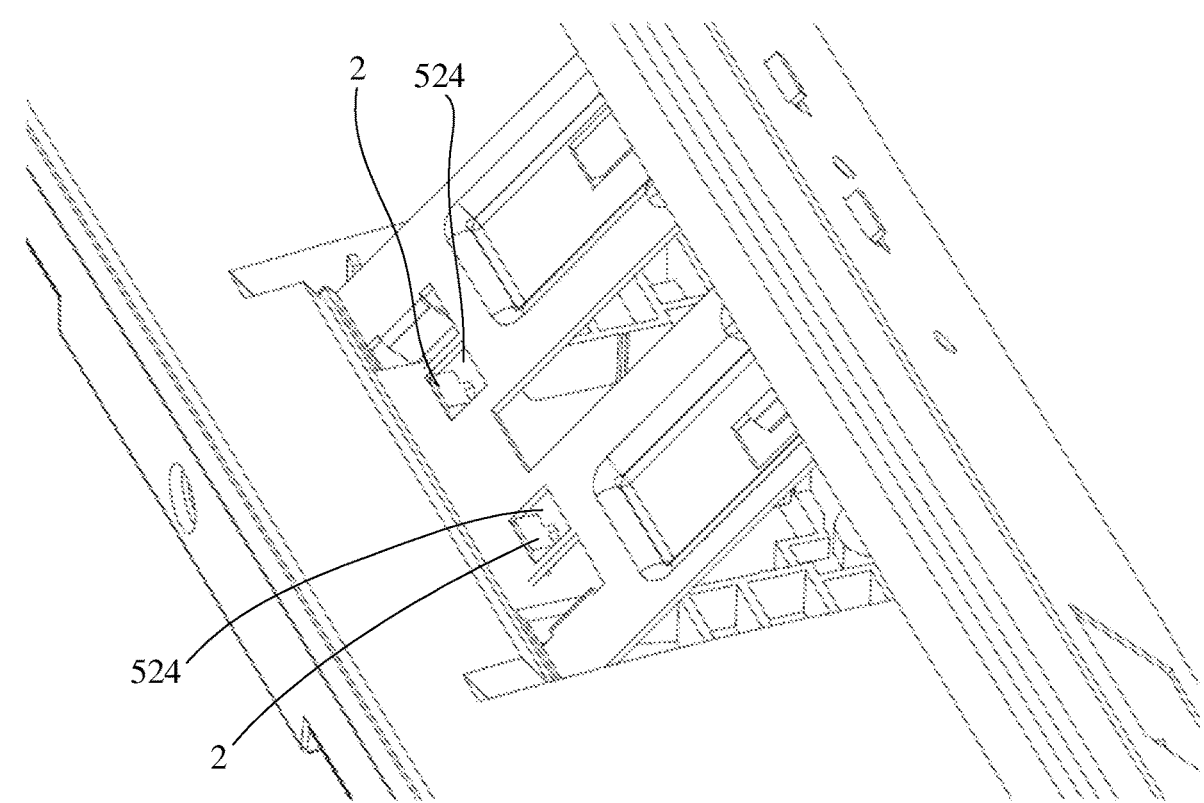
FIG. 15 is a partial enlarged view of part IV in FIG. 14.

FIG. 8 is a schematic perspective view of the shielding cover and the rear cover in an assembled state according to some exemplary embodiments of the present disclosure, and FIG. 9 is a partial enlarged view of part II in FIG. 8. FIG. 14 is a combined schematic view of the shielding cover and the rear cover prior to flipping according to some exemplary embodiments of the present disclosure, and FIG. 15 is a partial enlarged view of part IV in FIG. 14.

Referring to FIG. 8 and FIG. 9 in conjunction, the shielding cover 5 may be positioned and connected to the rear cover 1 to achieve the assembly of the two. Specifically, the shielding cover body 51 may be received by the first concave portion 151, and the shielding cover accessory 52 may be received by the second concave portion 152.

The two hook structures 2 of the rear cover 1 may be matched with the two card slots 524 of the shielding cover accessory 52, respectively, so as to achieve the positioning and connection between the shielding cover 5 and the rear cover 1. Specifically, when assembling the rear cover 1 and the shielding cover 5, the hook structure 2 may be aligned with the card slot 524 first, so that the hook structure 2 passes through the card slot 524. As shown in FIG. 14 and FIG. 15, at this time, the shielding cover 5 may form a certain inclination angle relative to the rear cover 1 to facilitate the insertion of the hook structure 2 into the card slot 524. Then, a joint of the shielding cover 5 and hook of the rear cover 1 is taken as a center, the shielding cover 5 is turned over and placed on the rear cover 1, and as shown in FIG. 8, the shielding cover 5 and the rear cover 1 are fixed together by fixing elements such as screws. In the embodiments of the present disclosure, when assembling the shielding cover and the rear cover, the hook structure may be used to align the card slot for pre-positioning, and there is no need to manually adjust a relative position of the shielding cover and the rear cover, which is beneficial to improve a positioning accuracy during assembly, and reduce a positioning deviation.

It should be understood that an area of an orthographic projection of the hook structure 2 on the second concave bottom 1525 is smaller than an area of an orthographic projection of the card slot 524 on the second concave bottom 1525, so that the hook structure 2 may pass through the card slot 524.

Further, the flat bottom 5211 of the shielding cover accessory 52 abuts against the positioning bottom 16 of the rear cover 1. That is, the shielding cover accessory 52 is in combination with the rear cover 1 through surface contacting, so as to ensure a parallelism of the shielding cover accessory 52, which is conductive for a more stable installation of the shielding cover 5, and avoids a phenomenon of the shielding cover tilting.

The plurality of recesses 5212 of the shielding cover accessory 52 are received by the plurality of receiving portions 18 of the rear cover 1, respectively. Parts of the flat bottom 5211 of the shielding cover accessory 52 located on two sides abut against the supporting ribs 19 on two sides, respectively. In this way, a more stable support may be provided to the shielding cover accessory 52.

For example, the plurality of second connecting holes 529 of the shielding cover accessory 52 are aligned with the plurality of third connecting holes 1527 of the rear cover, respectively, so as to facilitate the insertion of the fixing elements such as screws.

Optionally, referring to FIG. 8, the rear cover 1 may further include a plurality of heat dissipation holes HL1 on the concave sidewall 1513, and the shielding cover 5 may further include a plurality of heat dissipation holes HL2 on the shielding cover sidewall 513. For example, the plurality of heat dissipation holes HL1 and HL2 are distributed in an array. The plurality of heat dissipation holes HL1 on the rear cover 1 at least partially overlap with the plurality of heat dissipation holes HL2 on the shielding cover 5. In this way, by arranging a large number of heat dissipation holes, heat generated by the main circuit board may be transferred to the rear cover and the shielding cover of the display device through the heat dissipation holes and then taken away through heat exchange with air outside the rear cover during an operating process of the display device, thus preventing a normal operation of the main circuit board from being affected. For example, the plurality of heat dissipation holes may be evenly distributed, and distances between two adjacent heat dissipation holes may be approximately the same. In this way, the heat generated may be uniformly dissipated, and local overheating may be avoided, thereby improving a service life of the main circuit board.

Figure 10:
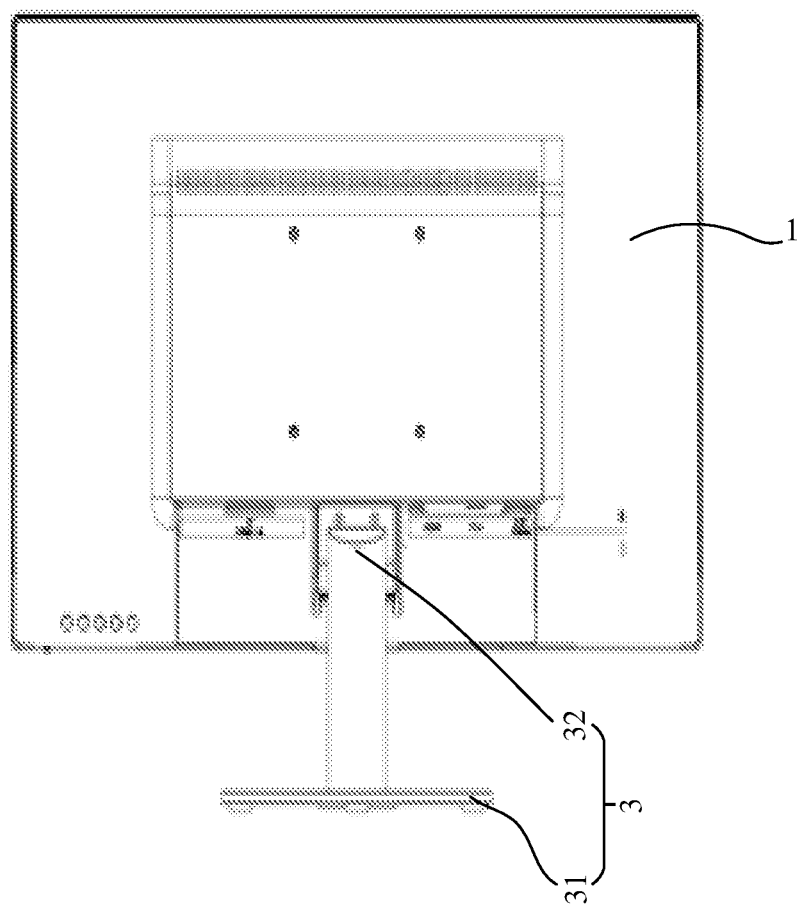
FIG. 10 is a rear view of a display device according to some exemplary embodiments of the present disclosure, wherein a rear cover, a shielding cover and a base of the display device are in an assembled state.
Figure 11:
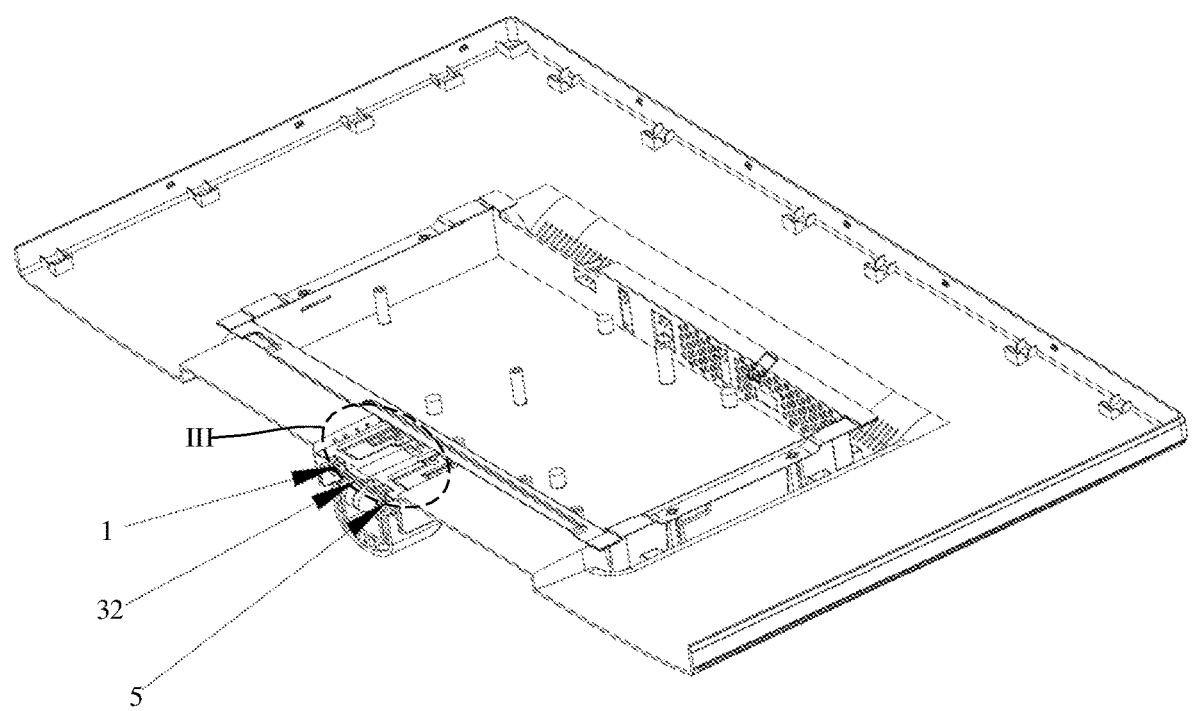
FIG. 11 is a perspective view of a rear cover, a shielding cover and a base of a display device in an assembled state, wherein a positional relationship between the rear cover, the shielding cover and the base is schematically shown.
Figure 12:
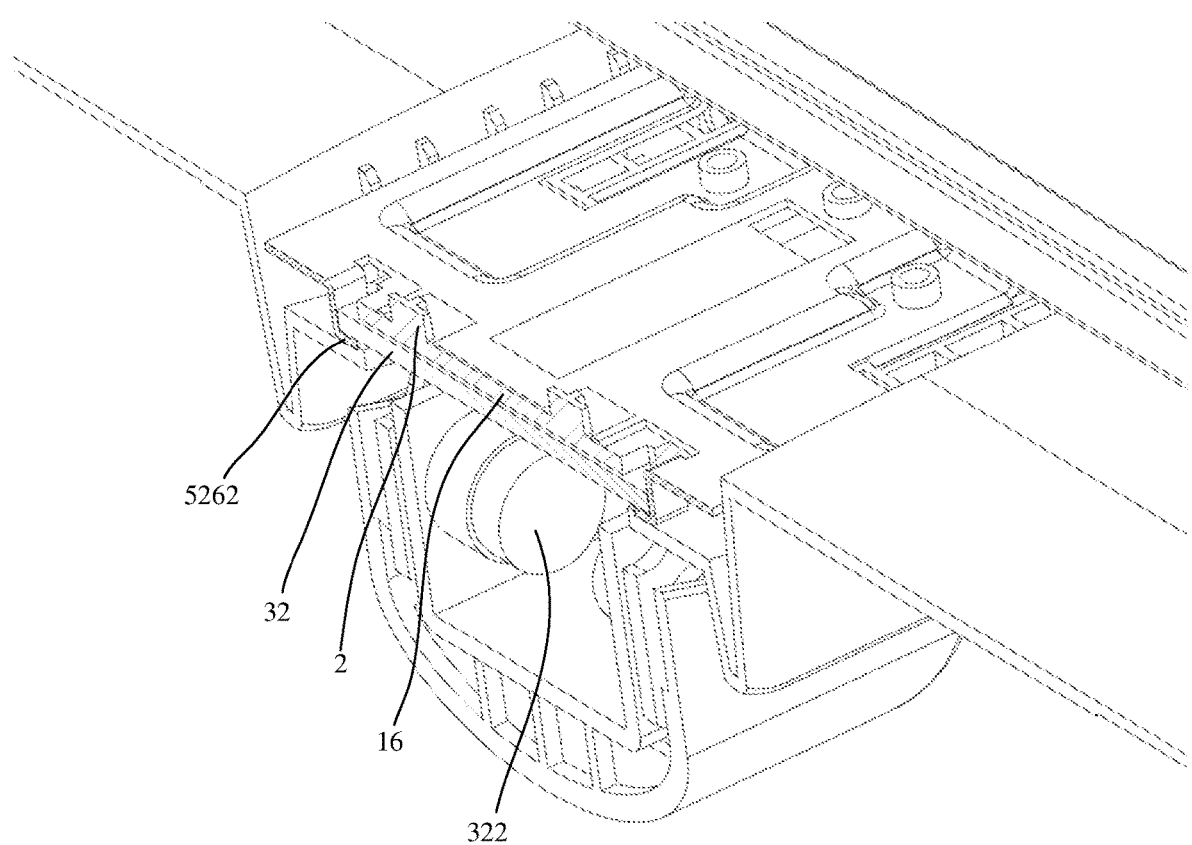
FIG. 12 is a partial enlarged view of part III in FIG. 11.

FIG. 10 is a rear view of the display device according to some exemplary embodiments of the present disclosure, wherein the rear cover, the shielding cover and the base of a display device are in an assembled state. FIG. 11 is a perspective view of the rear cover, the shielding cover and the base of the display device in the assembled state, wherein a positional relationship between the rear cover, the shielding cover and the base is schematically shown. FIG. 12 is a partial enlarged view of part III of FIG. 11;

Referring to FIG. 1 and FIGS. 10 to 12, the base 3 may include a base plate 31 and a bracket 32. The display device 100 may be placed on a supporting surface such as a desktop through the base plate 31. The bracket 32 may be connected and fixed to the shielding cover 5, so as to achieve a connection and fixing between the rear cover 1, the shielding cover 5 and the base 3.

A part of the bracket 32 may be positioned between the rear cover 1 and the shielding cover 5. For example, a part of the bracket 32 may be positioned between the positioning bottom 16 of the rear cover 1 and the two limiting portions 526 and 528 of the shielding cover accessory 52. In the embodiments of the present disclosure, as described above, the shielding cover accessory 52 is combined with the rear cover 1 through surface contacting, so as to ensure the parallelism of the shielding cover accessory 52, which is conductive for the more stable installation of the shielding cover 5 and avoids the phenomenon of the shielding cover tilting. In this way, it is beneficial for a part of the bracket 32 to be smoothly inserted between the rear cover and the shielding cover, and a difficulty of inserting and withdrawing caused by the tilting of the shielding cover is avoided.

Referring back to FIG. 6, the pair of first limiting portions 526 are arranged at an interval in the X direction, and the pair of second limiting portions 528 are arranged at an interval in the X direction. A part of the bracket 32 may be inserted into a space defined by the pair of first limiting portions 526 and the pair of second limiting portions 528. A movement of the bracket 32 in the X direction may be limited by the limiting sidewalls 5261 of the first limiting portions 526 and the limiting sidewalls 5281 of the second limiting portions 528. A movement of the bracket 32 in the Z direction may be limited by the limiting bottom walls 5262 of the first limiting portions 526, the limiting bottom walls 5282 of the second limiting portions 528 together with the positioning bottom 16 of the rear cover 1.

A movement of the bracket 32 in the Y direction may be limited by a part of the bracket 32 being inserted into the plurality of limiting holes 531 of the shielding cover accessory 52.

Through such a connection and fixing manner, the bracket 32 is connected and fixed to the shielding cover 5 made of metal, through which the fixing of the bracket 32 may be more stable. Moreover, the movements of the bracket 32 in each direction may be limited, through which the fixing of the bracket 32 may be more stable.

It should be understood that the bracket 32 may further include structures such as a rotating shaft 322, etc., so that the display panel may be rotated under a support of the bracket 32.

For example, the display device 100 may be any product or component with a display function, such as a smart phone, a wearable smart watch, smart glasses, a tablet computer, a television, a display, a digital photo frame, a navigator, a car monitor, an e-book, etc.

Although some embodiments of the general inventive concept of the present disclosure have been illustrated and described, those of ordinary skill in the art will understand that these embodiments may be changed without departing from the principle and the spirit of the general inventive concept of the present disclosure, and the scope of the present disclosure is defined by the claims and their equivalents.

What is claimed is:

1. A shielding cover, comprising:
   a shielding cover body, wherein the shielding cover body comprises a shielding cover body bottom, a first shielding cover sidewall, a second shielding cover sidewall, a third shielding cover sidewall and a fourth shielding cover sidewall, and the first shielding cover sidewall, the second shielding cover sidewall, the third shielding cover sidewall and the fourth shielding cover sidewall are perpendicular to the shielding cover body bottom, respectively; and a shielding cover accessory, wherein the shielding cover accessory is fixedly connected to the shielding cover body, and the shielding cover accessory comprises:
an accessory bottom comprising a flat bottom;
a connecting arm, wherein the shielding cover accessory is connected to the first shielding cover sidewall of the shielding cover body through the connecting arm; and
a positioning arm, wherein the connecting arm and the positioning arm are connected to two opposite ends of the accessory bottom, and the connecting arm and the positioning arm are configured to protrude in opposite directions from the accessory bottom, wherein the shielding cover accessory further comprises a plurality of card slots, the plurality of card slots are arranged at positions of the flat bottom close to the positioning arm, each card slot is configured to penetrate the flat bottom in a direction perpendicular to the flat bottom, and the plurality of card slots are arranged at intervals in a direction parallel to an extending direction of the positioning arm; and wherein the accessory bottom and the positioning arm are located on a side of the connecting arm away from the shielding cover body.

2. The shielding cover according to claim 1, wherein a shape of an orthographic projection of each card slot on the flat bottom has a rectangular shape, each card slot has a first size in a direction parallel to the extending direction of the positioning arm and a second size in a direction perpendicular to the extending direction of the positioning arm, and the first size is greater than the second size.

3. The shielding cover according to claim 2, wherein the shielding cover accessory further comprises a plurality of first openings arranged on the flat bottom, each first opening is configured to penetrate the flat bottom in the direction perpendicular to the flat bottom, and the plurality of first openings are arranged at intervals in the direction parallel to the extending direction of the positioning arm.

4. The shielding cover according to claim 3, wherein the plurality of first openings are respectively arranged adjacent to the plurality of card slots, and a spacing distance among the plurality of first openings in the direction parallel to the extending direction of the positioning arm is greater than a spacing distance among the plurality of card slots in the direction parallel to the extending direction of the positioning arm.

5. The shielding cover according to claim 4, wherein the shielding cover accessory further comprises a plurality of first limiting portions, each first limiting portion and the connecting arm are configured to protrude in a same direction relative to the flat bottom, and the plurality of first limiting portions are respectively arranged at the plurality of first openings.

6. The shielding cover according to claim 5, wherein each first limiting portion comprises a first limiting sidewall and a first limiting bottom wall, the first limiting sidewall is perpendicular to the flat bottom, and the first limiting bottom wall is parallel to the flat bottom;
the first opening has a first opening sidewall away from the card slot adjacent to the first opening, and the first limiting sidewall is connected to the first opening sidewall; and
the first limiting bottom wall is connected to the first limiting sidewall, and the first limiting bottom wall is configured to extend toward the card slot adjacent to the first limiting bottom wall.

7. The shielding cover according to claim 6, wherein the accessory bottom further comprises a plurality of recesses, the plurality of recesses and the connecting arm are configured to protrude in a same direction relative to the flat bottom, and the plurality of recesses are arranged at intervals in the direction parallel to the extending direction of the positioning arm; the shielding cover accessory further comprises a plurality of second openings, and the plurality of second openings are respectively arranged in the plurality of recesses.

8. The shielding cover according to claim 7, wherein the shielding cover accessory further comprises a plurality of second limiting portions, the plurality of second limiting portions and the plurality of first limiting portions are configured to protrude in the same direction relative to the flat bottom, and the plurality of second limiting portions are respectively arranged at the plurality of second openings.

9. The shielding cover according to claim 8, wherein each second limiting portion comprises a second limiting sidewall and a second limiting bottom wall, the second limiting sidewall is perpendicular to the flat bottom, and the second limiting bottom wall is parallel to the flat bottom;
the second opening has a second opening sidewall close to a center of the shielding cover accessory, and the second limiting sidewall is connected to the second opening sidewall; and
the second limiting bottom wall is connected to the second limiting sidewall, and the second limiting bottom wall is configured to extend toward the center of the shielding cover accessory.

10. The shielding cover according to claim 1, wherein the shielding cover accessory comprises a plurality of first connecting holes, the plurality of first connecting holes are arranged on the connecting arm, and the plurality of first connecting holes are arranged at intervals in the direction parallel to the extending direction of the connecting arm.

11. The shielding cover according to claim 10, wherein the shielding cover accessory further comprises a plurality of limiting holes, the plurality of limiting holes are arranged on the connecting arm, and each limiting hole is located between two adjacent first connecting holes.

12. A display device, comprising:
the shielding cover according to claim 1; and
a rear cover connected to the shielding cover.

13. The display device according to claim 12, wherein the rear cover comprises a plurality of hook structures, and the plurality of hook structures are respectively matched with the plurality of card slots of the shielding cover.

14. The display device of claim 13, wherein the rear cover comprises:
a first concave portion configured to receive the shielding cover body;
a second concave portion configured to receive the shielding cover accessory; and
a positioning bottom and a connecting sidewall arranged in the second concave portion;
wherein the first concave portion has a first concave bottom and four concave sidewalls, the second concave portion has a second concave bottom, a first concave sidewall, a second concave sidewall, a third concave sidewall and a concave opening, the first concave sidewall is opposite to the concave opening, the second concave sidewall is opposite to the third concave sidewall, and the first concave portion is communicated with the second concave portion through the concave opening; and the positioning bottom has a flat surface, a side of the positioning bottom is connected to the second concave bottom through the connecting sidewall, and the other side of the positioning bottom is connected to the first concave sidewall.

15. The display device according to claim 14, wherein each hook structure comprises:

a body portion, wherein the body portion is configured to protrude toward the shielding cover relative to the positioning bottom; and a hook portion, wherein an end of the hook portion is connected to the body portion, and the hook portion is configured to protrude in a direction toward the first concave sidewall relative to the body portion.

16. The display device according to claim 15, wherein the hook portion is spaced from the positioning bottom by a first distance in a direction perpendicular to the positioning bottom, and the first distance is greater than a thickness of the flat bottom of the shielding cover in a direction perpendicular to the positioning bottom.

17. The display device according to claim 15, wherein the hook portion has a chamfered portion, the chamfered portion is arranged at an edge of the hook portion facing the first concave sidewall and the positioning bottom, each hook structure further comprises a reinforcing rib arranged on a side of the body portion away from the hook portion.

18. The display device according to claim 17, wherein an area of an orthographic projection of each hook structure on the positioning bottom is smaller than an area of an orthographic projection of each card slot on the positioning bottom.

19. The display device according to claim 15, wherein the flat bottom of the shielding cover accessory is abutted against the positioning bottom of the rear cover;

wherein the accessory bottom of the shielding cover accessory further comprises a plurality of recesses, the plurality of recesses and the connecting arm are configured to protrude in the same direction relative to the flat bottom, and the plurality of recesses are arranged at intervals in the direction parallel to the extending direction of the positioning arm; and the rear cover further comprises a plurality of receiving portions, the plurality of receiving portions are respectively located on two sides of the positioning bottom, and the plurality of receiving portions are configured to respectively receive the plurality of recesses of the shielding cover accessory;

wherein the rear cover further comprises a first set of supporting ribs located between the second concave sidewall and one of the receiving portions, and a second set of supporting ribs located between the third concave sidewall and another one of the receiving portions, and each of the first set of supporting ribs and the second set of supporting ribs comprises a plurality of supporting ribs;

wherein the display device further comprises a base comprising a bracket, and a part of the bracket is positioned between the shielding cover accessory and the rear cover.

20. The display device according to claim 19, wherein the shielding cover accessory comprises a plurality of first limiting portions and a plurality of second limiting portions, and each of the plurality of first limit portions and the plurality of second limit portions comprises a limiting sidewall and a limiting bottom wall, a part of the bracket is positioned between the positioning bottom of the rear cover and the limiting bottom wall, so as to limit a movement of the bracket in the direction perpendicular to the positioning bottom, and a part of the bracket is further positioned between the limiting sidewalls of the plurality of first limiting portions and between the limiting sidewalls of the plurality of second limiting portions, so as to limit a movement of the bracket in a direction perpendicular to the limiting sidewall.

\* \* \* \* \*